US011110260B1

(12) United States Patent
Shadduck

(10) Patent No.: US 11,110,260 B1
(45) Date of Patent: Sep. 7, 2021

(54) SYSTEMS AND METHODS FOR APPLYING MEDIA TO SKIN

(71) Applicant: Hermes Innovations, LLC, San Jose, CA (US)

(72) Inventor: John H. Shadduck, Menlo Park, CA (US)

(73) Assignee: Hermes Innovations, LLC, San Jose, CA (US)

( * ) Notice: Subject to any disclaimer, the term of this patent is extended or adjusted under 35 U.S.C. 154(b) by 0 days.

(21) Appl. No.: 17/010,161

(22) Filed: Sep. 2, 2020

(51) Int. Cl.
*A61M 35/00* (2006.01)
*A61M 37/00* (2006.01)
*A61N 5/06* (2006.01)

(52) U.S. Cl.
CPC ...... *A61M 37/0092* (2013.01); *A61M 35/003* (2013.01); *A61N 5/062* (2013.01); *A61M 2037/0007* (2013.01); *A61M 2205/05* (2013.01); *A61M 2205/051* (2013.01); *A61M 2205/075* (2013.01); *A61M 2205/3317* (2013.01); *A61M 2205/3337* (2013.01); *A61M 2205/75* (2013.01); *A61M 2210/04* (2013.01); *A61M 2210/0625* (2013.01); *A61N 2005/0651* (2013.01)

(58) Field of Classification Search
CPC .. A61M 37/00; A61M 35/00; A61M 37/0092; A61M 35/003; A61M 2037/0007; A61M 2205/05; A61M 2205/051; A61M 2205/3317; A61M 2205/3337; A61M 2205/75; A61M 2210/04; A61M 2210/0625; A61N 5/0616; A61N 5/0617; A61N 5/06; A61N 2005/065; A61N 2005/0651

See application file for complete search history.

(56) References Cited

U.S. PATENT DOCUMENTS

| | | | |
|---|---|---|---|
| 8,714,853 B2 | 5/2014 | Sutcliffe et al. | |
| 8,939,669 B2 | 1/2015 | Le et al. | |
| 8,968,221 B2 | 3/2015 | Pryor et al. | |
| 9,119,758 B2 | 9/2015 | Ho | |
| 10,179,229 B2 | 1/2019 | Ignon et al. | |
| 2008/0254006 A1* | 10/2008 | Hantash | A61P 17/14 424/93.7 |
| 2008/0262394 A1* | 10/2008 | Pryor | A61N 5/0619 601/15 |
| 2009/0036845 A1* | 2/2009 | Smith | A61K 9/0014 604/289 |
| 2015/0045723 A1* | 2/2015 | Paithankar | A61P 17/10 604/22 |
| 2016/0051436 A1* | 2/2016 | Rosario | A61N 5/0624 601/6 |
| 2016/0074641 A1* | 3/2016 | Mehta | A61M 35/003 604/290 |
| 2019/0192873 A1* | 6/2019 | Schwarz | A61F 7/00 |

* cited by examiner

*Primary Examiner* — Jason E Flick
(74) *Attorney, Agent, or Firm* — Levine Bagade Han LLP

(57) ABSTRACT

Methods and devices related to the fields of skin care, hair restoration and lip care wherein the systems may be used by an individual for infusing treatment media into skin or lips for cosmetic and rejuvenation purposes, hair restoration purposes or other therapeutic purposes.

30 Claims, 27 Drawing Sheets

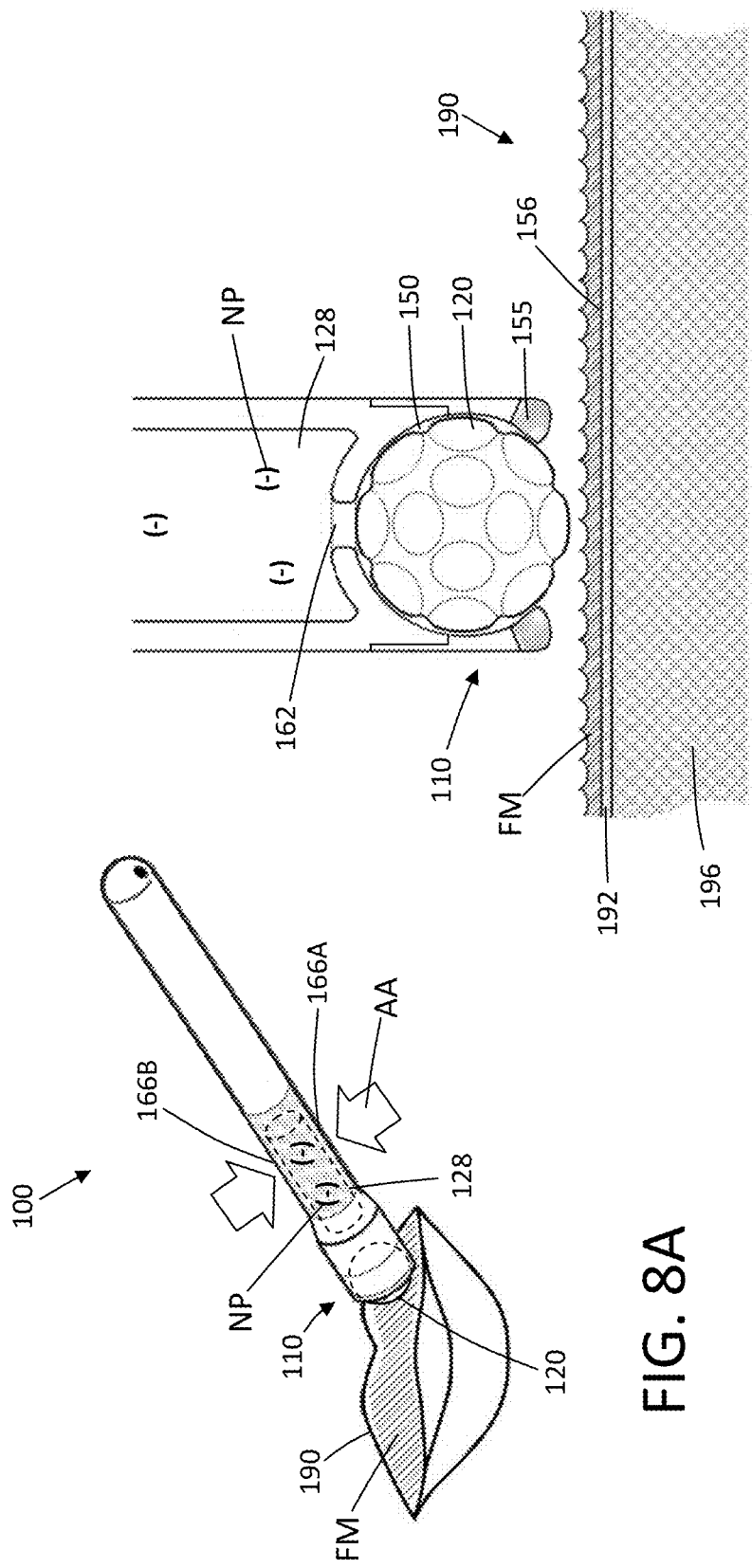

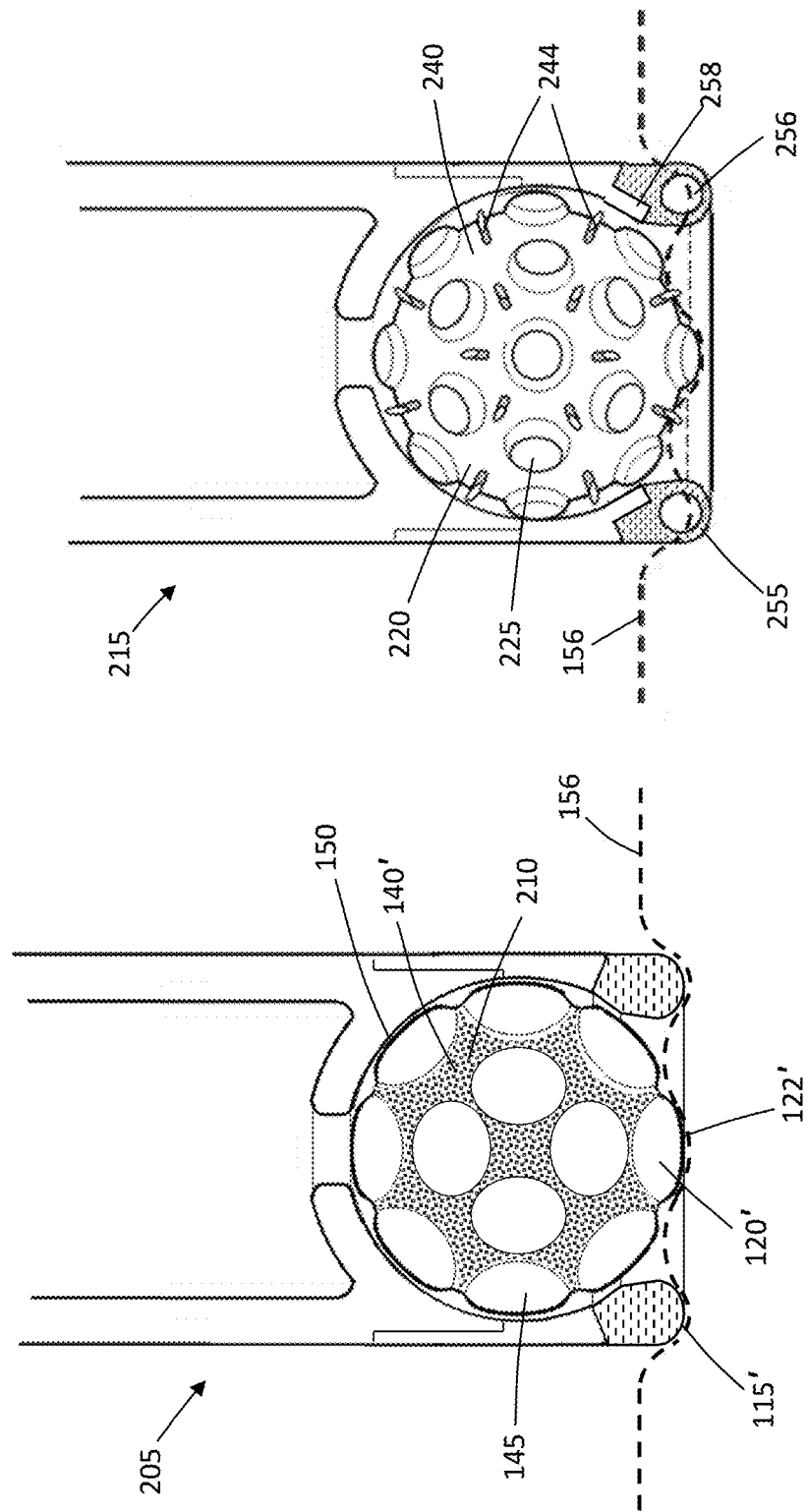

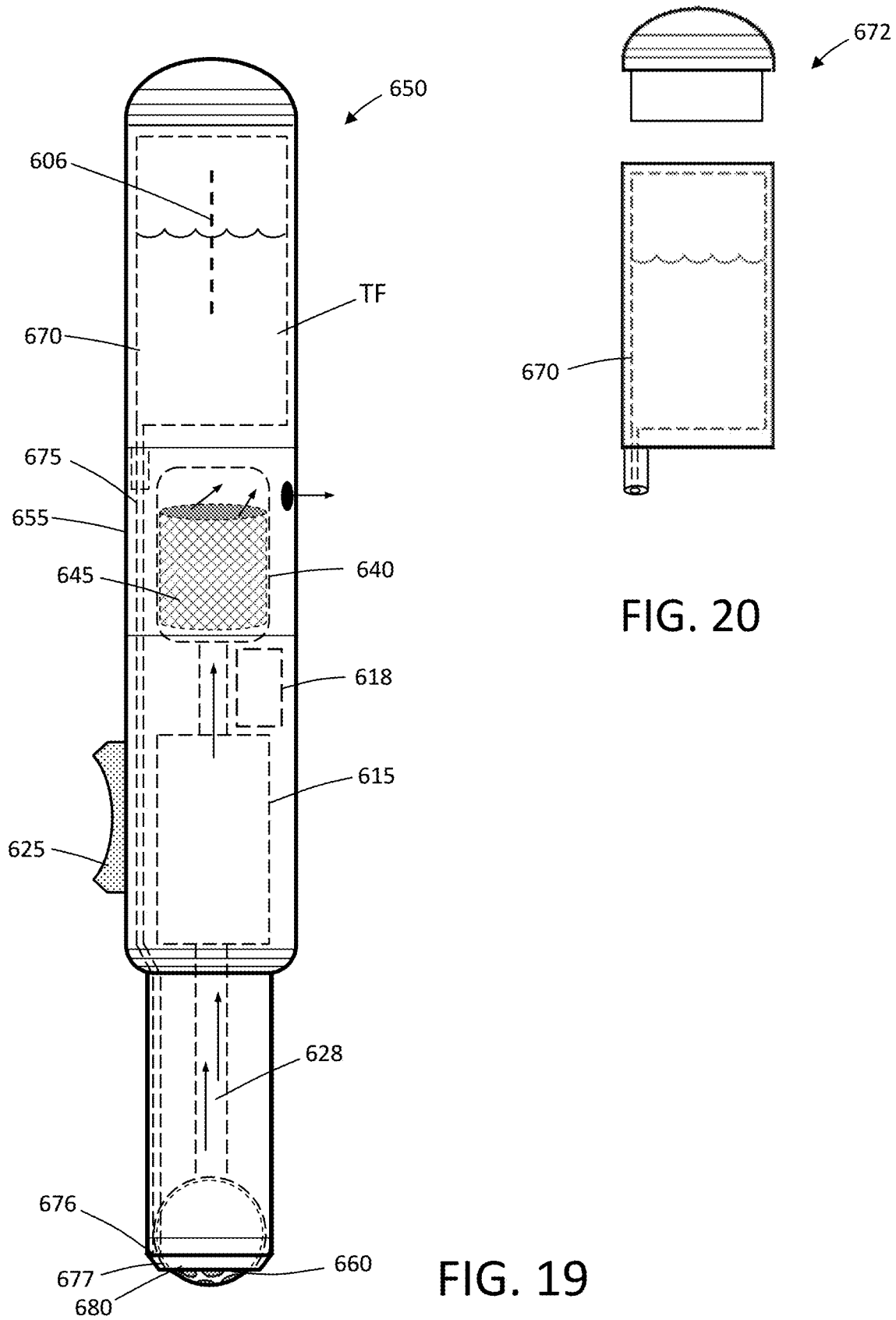

SYSTEMS AND METHODS FOR APPLYING MEDIA TO SKIN

BACKGROUND

The present invention relates to devices for treating a subject's skin or lips and more particularly to device that enhances absorption of treatment media into tissue for cosmetic and therapeutic purposes.

SUMMARY OF THE INVENTION

The applicator systems and methods corresponding to the invention relate in general to the fields of skin care, hair restoration and lip care wherein the systems may be used by an individual for infusing treatment media into his or her skin or lips for cosmetic and rejuvenation purposes, hair restoration purposes or other therapeutic purposes.

The present disclosure includes devices for enhancing fluid delivery to a subject's skin or lips. For example, one variation of such a device includes an applicator body extending about a longitudinal axis from a proximal end to a distal applicator tip; a rolling member carried in a receiving space of the applicator tip; and a negative pressure mechanism communicating with a flow pathway in the applicator tip for applying negative pressure to tissue engaged by the applicator tip.

A variation of the device can include the applicator body having a distal periphery and where the rolling member and the distal periphery are configured to contact tissue during use. The distal periphery can be configured to create a seal against the tissue during use.

In an additional variation, an exposed portion of the rolling member extends distally from the distal periphery less than 25% of the diameter of the rolling member.

Variations of the rolling member can have a non-smooth surface. Alternatively, or in combination, the surface of the rolling member can be a first surface portion defining a spherical rotational envelope and a second surface portion comprising surface discontinuities. The flow pathway can comprise the surface discontinuities in the rolling member. In some variations, the surface discontinuities comprise at least one of recesses, channels, grooves, notches, facets, bores and porosities.

Variations of the device can include the first surface portion defining a selected surface area that allows the rolling member to roll smoothly in a cooperating surface of the receiving space. In some examples, the first surface portion has surface area of at least 40% of the surface area of said spherical rotational envelope of the rolling member.

The variations of the device can include a second surface portion having a surface area of at least 10% of the surface area of said spherical rotational envelope of the rolling member.

In additional variations, the surface of the rolling member can include recessed portions and adjacent projecting portions. Variations of the projecting portions can have a sharp apex. Alternatively, or in combination, a projecting portion can comprise a needle. In yet additional variations, at least a portion of the rolling member has an abrasive surface.

The devices described herein can include a distal periphery that comprises at least one of a resilient material and a lubricious material. The distal periphery can also include an abrasive surface.

The negative pressure mechanisms used herein can comprise any vacuum source. For example, one variation includes a positive displacement pump. In additional variations, the negative pressure mechanism is adapted for manual actuation.

The devices described herein can further comprise a valve in the flow pathway.

In additional variations, the devices can have an applicator body that includes at least first and second detachable elements that when detached allow for removal of the rolling member.

Variations of the applicators can carry at least one LED and a rolling member that is at least partly transparent material.

The devices can also include flow pathway, which comprises surface discontinuities in surface of the receiving space.

The invention described herein also includes methods for treating a subject's skin or lips. For example, one such method includes contacting a tissue surface with a rolling member carried at a distal end of an applicator body; moving the rolling member over the tissue surface; and creating negative pressure about the rolling member in contact with the tissue surface to transiently cause negative pressure in subsurface tissue to enhance permeability of the tissue surface.

The methods described herein can further include applying a treatment media to the tissue surface. In some variations, the moving step manipulates tissue to thereby enhance penetration of the treatment media therein. Alternatively, or in combination, the moving step includes the surface discontinuities of the rolling member causing at least one of compressing, stretching, tensioning and piercing the tissue surface.

In an additional variation, the method includes a creating step, which suctions treatment media in a circuitous path over the tissue surface about the surface discontinuities to thereby enhance penetration of the treatment media therein.

The methods can also include a distal periphery of the applicator body that contacts tissue to seal the negative pressure around the rolling member as it moves over the tissue surface.

In another variation of a method, the moving step abrades the tissue surface with an abrasive surface of the applicator body to thereby enhance penetration of the treatment media therein.

Another variation of a method disclosed herein includes a method for treating hair loss in a targeted tissue of a subject. For example, such a method can include applying a treatment media configured to aid in hair growth to targeted tissue of the subject; contacting the tissue with an applicator; and drawing a negative pressure about the applicator when in contact with the tissue to transiently apply the negative pressure in a subsurface tissue to enhancing penetration of the treatment media into the targeted tissue.

The treatment media applied to the targeted tissue can include any substance selected from the group consisting of finasteride, minoxidil, corticosteroid, dutasteride, psoralen and a combination thereof.

In certain variations, the method includes pulsing the negative pressure. The negative pressure can comprise actuating a vacuum pump mechanism.

In additional variations, the method can further include manipulating the targeted tissue with the applicator to enhance penetration of the treatment media therein. Manipulating the targeted tissue can include at least one of compressing, stretching, tensioning, exfoliating and piercing a tissue surface with a surface features of the applicator. Additionally, a variation includes an applicator having a rolling member and manipulating the targeted tissue comprises rolling the rolling member on the targeted tissue.

In additional variations, the method can include providing the negative pressure through a flow path around the rolling member.

In an additional variation, application of the negative pressure causes a suction of treatment media in a circuitous path over the targeted tissue about a surface feature of the rolling member to enhance penetration of the treatment media in the targeted tissue.

Variations of the applicator can further comprise moving the applicator over the targeted tissue. For example, the applicator can include a rolling member, where moving the applicator comprises rolling the rolling member on the targeted tissue to exfoliate the targeted tissue with a surface feature of the rolling member to enhance penetration of the treatment media in the targeted tissue.

In additional variations of the method, a distal periphery of the applicator body contacts tissue to seal the negative pressure over the targeted tissue.

The methods described herein can further include irradiating the targeted tissue with light wavelengths from a light emitter carried by the applicator. Alternatively, or in addition, the methods can further apply energy from an ultrasound emitter to the tissue, where the ultrasound emitter is carried by the applicator.

The present disclosure also includes variations of devices for treatment of a subject's skin or lips. One such example includes an applicator body having a distal applicator tip; the applicator tip including an inflow path channel and an outflow path; a liquid media source in communication with the inflow path; a negative pressure source in communication the outflow path; and a collector in the outflow path adapted to capture liquid media from a flow therein.

A variation of the device includes a collector that comprises a cyclonic mechanism, a baffle arrangement, a filter, or a combination thereof. Variations of the device can include an applicator body that carries a pump comprising the negative pressure source, or a reservoir comprising the liquid media source.

Another variation of a method includes a method for treating a subject's skin. For example, such a method can include providing an applicator carries a motor-driven pump assembly for providing negative pressure in the applicator; applying treatment media to targeted skin of a subject; contacting the tissue with an applicator to manipulate the targeted skin; and drawing negative pressure about the applicator while in contact with the targeted tissue to transiently cause negative pressure in a subsurface tissue to enhance penetration of the treatment media into the targeted tissue.

A variation of the method can include manipulating the targeted skin includes at least one of compressing, stretching, tensioning, exfoliating and piercing the tissue surface with the applicator.

The applicator can further include a rolling member at a distal end of the applicator and where manipulating the targeted skin comprises rolling the rolling member over a surface of the targeted tissue.

It will be understood that other objects and purposes of the invention, and variations thereof, will be apparent upon reading the following specification and inspecting the accompanying drawings. These and other features, aspects and advantages of the present invention will become better understood with reference to the following drawings.

BRIEF DESCRIPTION OF THE DRAWINGS

FIG. 8A illustrates a first step in a method of the invention where the subject applies a treatment media topically to lips and actuates the squeeze bulb to create negative pressure in the applicator.

FIG. 8B illustrates an enlarged view of the step in the method of FIG. 8A where the applicator tip is prepared for contact with flowable treatment media applied topically to the tissue surface.

FIG. 9 is a cut-away view of another variation of applicator tip similar to that of FIG. 1 where the rolling member includes abrasive portions for providing traction with tissue.

FIG. 10 is a cut-away view of yet another variation of applicator tip similar to that of FIG. 1 where the rolling member includes sharp micro-needles for providing traction with tissue and for causing penetrations in surface tissue.

FIG. 19 is an elevational view of another variation of an applicator with a distal rolling member wherein the applicator body carries a DC motor driven pump assembly, a filter, and a detachable fluid reservoir for carrying a treatment fluid.

FIG. 20 is an elevational view of the detachable fluid reservoir of FIG. 19

DETAILED DESCRIPTION OF THE INVENTION

Figure 1:
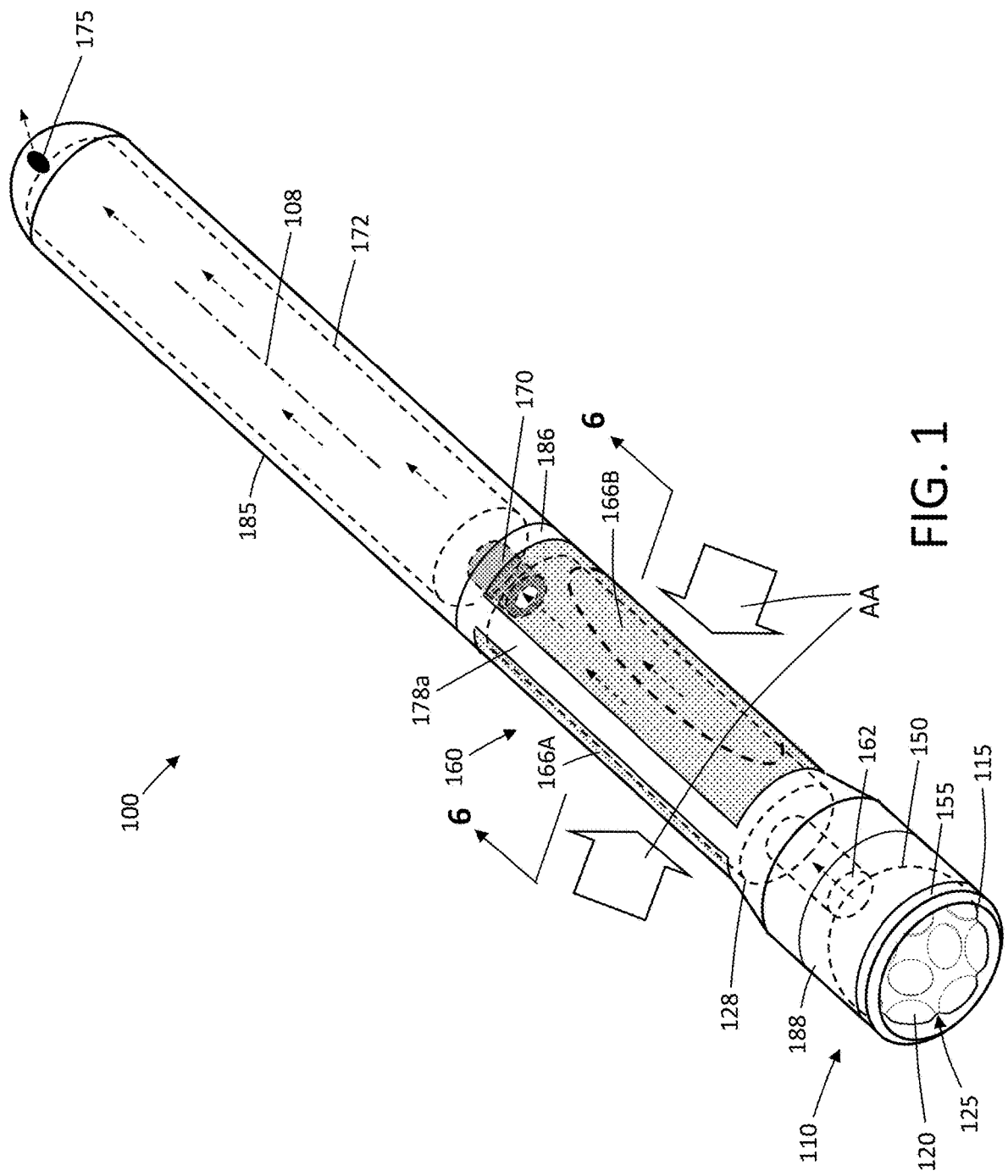
FIG. 1 is a perspective view of an embodiment of a treatment device or applicator corresponding to the invention adapted for enhancing fluid absorption by a subject's lips or skin, where a distal applicator tip includes a rolling member surrounded by a peripheral tissue-contacting element.

FIGS. 1, 3 and 5A-5B illustrate a system for treating skin or lips which comprises a hand-held treatment device or applicator 100 with a distal applicator tip 105 that is adapted for applying transient negative pressure to a skin surface to enhance fluid absorption and penetration into surface layers of a treatment site in a subject's skin or lips. The device or applicator 100 has a shaft or applicator body 106 extending about longitudinal axis 108 that is gripped with a subject's fingers for movement over a treatment site. The distal applicator tip or roller tip 105 defines a skin interface where the applicator body 106 has a distal housing 110 with a distal periphery 115 that surrounds or is adjacent to an exposed portion of a rolling member 120. As will be described below, the distal periphery 115 is configured to provide a seal against a tissue surface for the purpose of containing negative pressure around the rolling member 120 when in contact with a targeted treatment site.

As background, roller ball devices are well known in the art for applying cosmetic fluids, deodorants and the like to skin with a spherical roller ball that carries fluid from an interior chamber of an applicator to a skin surface as the roller ball contacts and rolls over a treatment site. As an example, FIG. 2 illustrates a typical prior art cosmetics roller ball as shown in U.S. Pat. No. 8,939,669 issued Jan. 27, 2015 to Son Q. Le et al, titled "Roller-Ball Applicator Assembly for Topical Oils Application" (see FIG. 1b in '669 with original reference numerals removed for convenience). As can be seen in FIG. 2, an important aspect of such prior art roller ball devices can be understood wherein the roller ball has a diameter D and the axial dimension A of the "exposed surface" (in sectional view) of the roller ball extends well beyond the distal tip of the device housing H and is a substantial fraction of the roller ball diameter D (referents D, A and H added by the author to the prior art figure). The large dimension A of the "exposed surface" of the roller ball is important for carrying fluids and applying such fluids to a subjects' skin. In such cosmetic roller ball applicators, the "exposed surface" dimension A as shown in FIG. 2 typically ranges from 25% to 40% of the roller ball diameter D. In such a prior art roller ball devices, the roller is exposed to an interior chamber of the assembly that carries a treatment liquid. Such a liquid interfaces with a surface of a rotating roller ball, which applies a film of the liquid to a subject's skin. As will be described below, the present invention differs entirely in that (i) there is no liquid contained in a chamber or channel that interfaces with the roller ball, and thus (ii) there is no liquid delivered by the roller ball to a subject's skin. In contrast, the present invention has an interior channel that interfaces with the rolling member, where such an interior channel communicates with a negative pressure source to suction or aspirate fluid around or through the rolling member into such an interior channel. This system allows the rolling member to be configured for skin manipulation rather than liquid delivery to a skin surface.

Figure 2:
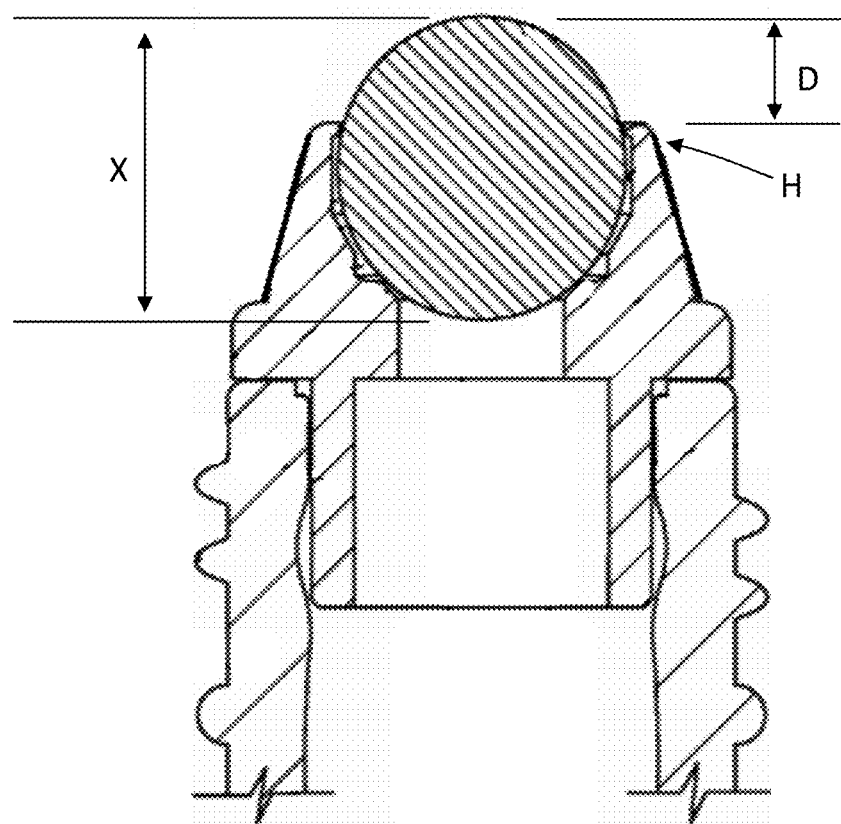
FIG. 2 is a sectional view of a prior art cosmetic roller ball device.
Figure 3:
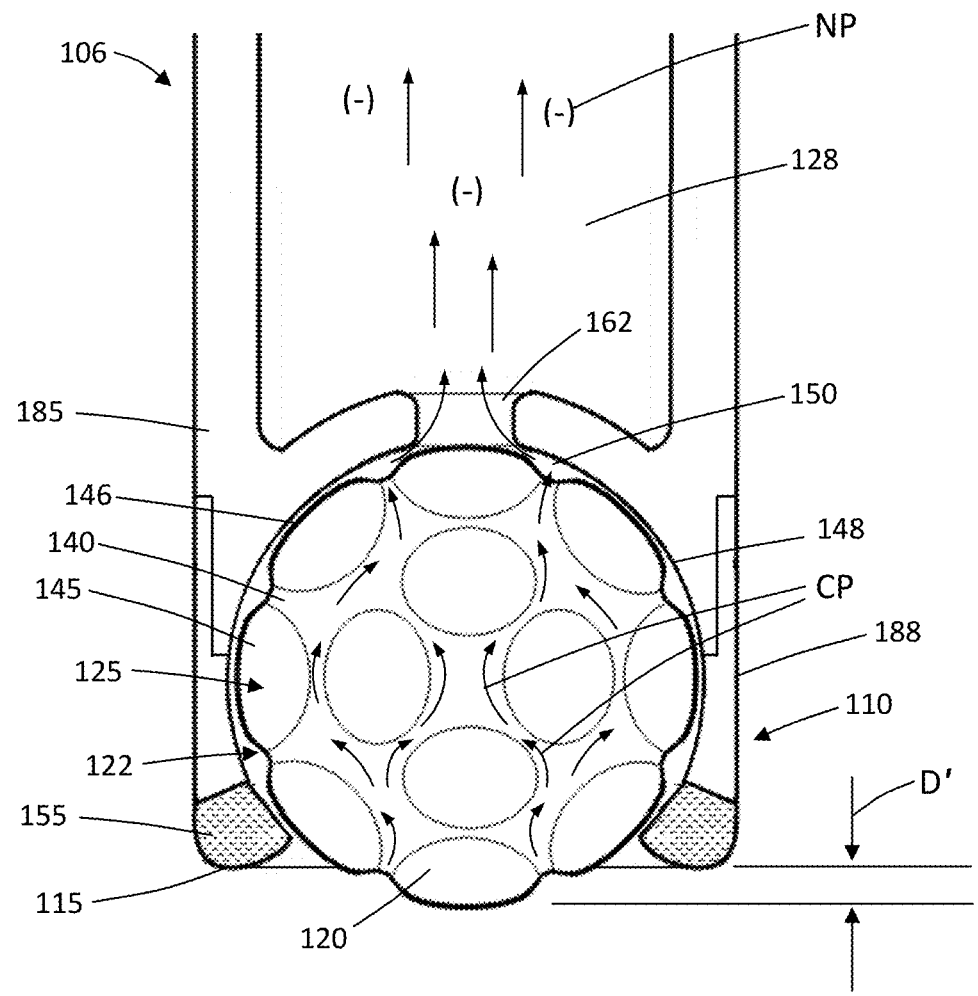
FIG. 3 is an enlarged cut-away view of the applicator tip of FIG. 1 showing the rolling member with discontinuities in the surface thereof for manipulating engaged tissue and for causing a circuitous path of fluid flows over a tissue surface when the rolling member is in contact with tissue.

Now turning to FIG. 3, a distal applicator tip 105 of the present invention is shown. As can be seen in FIG. 3, the applicator tip 105 carries a rolling member 120 in housing 110 that has a function that is entirely different from that of prior art cosmetic roller ball devices as in FIG. 2. In FIG. 3, the distal roller tip 105 is configured to apply negative pressure to a tissue surface—not a fluid. The fluid absorption aspect of the invention is a resulting effect of the negative pressure delivered to, and contained within, the distal applicator tip 105 when engaging a tissue surface. In the variation shown in FIG. 3, the rolling member 120 is not configured to contact and deliver fluid from an interior channel 128 of the device. The function of the rolling member 120 of the invention is to manipulate tissue in contact with the rolling member 120 which thereby allows fluid absorption and penetration into the tissue surface. The term tissue manipulation as used herein describes the effects of the rolling surface 122 of rolling member 120 that is configured with surface discontinuities 125 that engage tissue, where the effects can be described as, or include, stretching or tensioning tissue, compressing tissue, piercing tissue, indenting tissue or otherwise transiently modifying tissue from its natural state to a manipulated state as the surface discontinuities 125 of rolling member 120 engage the tissue surface under negative pressure to thereby transiently and locally increase the permeability of the skin surface layer. Of particular interest, the rolling member 120 thus is adapted to create the desired tissue manipulation effects in a friction-free manner as the rolling surface 122 and surface discontinuities 125 roll over a tissue surface.

Referring again to FIG. 3, the enlarged view of the rolling member 120 shows a rolling surface 122 that is not smooth but is configured surface discontinuities 125 that comprise first and second surface portions where the second surface consists of recessed portions or channels 140 around the first surface portion consisting of projecting portions 145. The recessed portions 140 provide a flow path for negative pressure NP in interior channel 128 to flow around the surface 122 of the rolling member 120. As will be described below, the negative pressure NP when in sealed contact with the patient's lips or skin can cause transient negative pressure within the engaged tissue to assist in rapid absorption or penetration of a fluid media into the engaged tissue. In the variation shown in FIG. 3, the rolling member 120 has a plurality of projecting portions 145 that may number from 10 to 1,000 or more where the outermost surfaces 146 of the projecting portions 145 define a spherical rotational envelope. Such outermost surface 146 rollably contacts the surface 148 of the receiving space 150 in the distal housing 110 of the applicator tip 105 that receives the rolling member 120. The term "spherical rotational envelope" as used herein describes the envelope in which the rolling member 120 contacts if it were rotated in all possible directions. As can be understood from FIG. 3, the number of projecting portions 145 are of a sufficient number to ensure that the rolling member 120 rolls or rotates smoothly in the receiving space 150. Typically, the first surface portion consisting of projecting portions 145 has surface area of at least 40% of the total surface area of the spherical rotational envelope of the rolling member 120. Further, the second surface portion consisting of the recessed portions 140 has a surface area of at least 10% of the total surface area of the spherical rotational envelope of the rolling member 120.

Still referring to FIG. 3, the surface discontinuities 125 are shown as channels, but other features can provide suitable flow pathways and fall within the scope of the invention, which includes notches, facets, recesses, grooves, partial bores, through-bores and porosities. Further, the projecting portions 145 may have outermost surfaces 146 that vary within a rolling member 120, for example, with some outermost surfaces 146 being flatter to allow smooth rotation and other outermost surfaces 146 having a sharp apex or a needle-like tip to penetrate tissue or to indent and stretch a tissue surface. As can be understood from FIG. 3, in one variation, the recessed portions or channels 140 are interconnected to thus provide circuitous pathways CP for aspirated fluid flows about the surface of the rolling member 120. Thus, when the rolling member 120 is in contact with tissue, a fluid treatment media under such negative pressure is drawn through the circuitous pathways CP to thereby cause such a fluid media to remain in contact with the tissue surface for a longer interval compared to a non-circuitous pathway. Thus, the surface discontinuities 125 are specifically configured to manipulate the tissue surface and provide a circuitous flow pathway, where the tissue manipulation can consist of stretching, indenting or tensioning tissue, compressing tissue, and piercing or penetrating tissue. At the same time, as will be described below, the negative pressure at the tissue surface can cause transient negative pressure in subsurface tissue to cause the rapid absorption and penetration of the fluid media into the engaged tissue.

Still referring to FIG. 3, in a variation, the distal housing 110 of applicator body 106 has a distal peripheral element 155 that defines the distal periphery 115 where the peripheral element 155 comprises a lubricious material such as Teflon or a resilient material such as silicone, or a combination of lubricious and resilient materials, suited for providing a seal against tissue as the distal periphery 115 and rolling member 120 are translated over a tissue surface to thereby contain negative pressure in the interface of the tissue and the distal applicator tip 105.

In FIG. 3, it also can be seen that the housing 110 of the present invention differs from a typical cosmetic roller ball device as in the prior art device of FIG. 2. In FIG. 3, the exposed portion of rolling member 120 extends distally beyond distal periphery 115 of the housing 110 a dimension D' which is much smaller than dimension D in the prior art device of FIG. 2. In FIG. 3, the exposed portion of rolling member 120 extends distally from distal periphery 115 less than 25% of the diameter of the rolling member 120, and often less than 20% of the diameter of the rolling member 120. In a variation, the exposed portion of rolling member 120 extends distally from distal periphery 115 less than 10% of the diameter of the rolling member 120. It can be understood that dimension D' is important so that the surface 122 of the rolling member 120 and discontinuities 125 therein contact and manipulate tissue while the distal periphery 115 contacts and provides a seal to capture the negative pressure about the skin surface and cause negative pressure in subsurface tissue as will be described further below. In another aspect, the exposed surface of the rolling member 120 extends distally from distal periphery 115 less than 5 mm and often is less than 3 mm.

Figure 4:
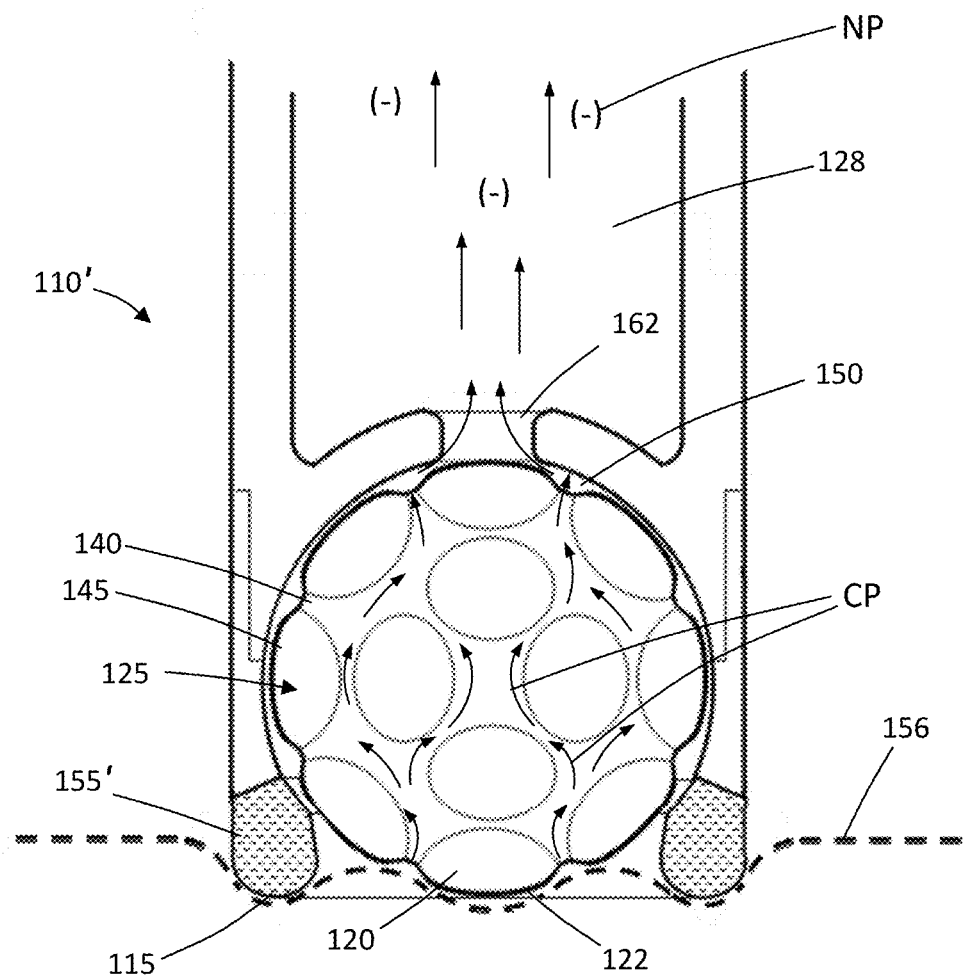
FIG. 4 is a cut-away view of a variation of an applicator tip similar to that of FIG. 3.

FIG. 4 illustrates a variation of a distal applicator tip 110' where the surface 122 of the rolling member 120 does not extend distally beyond the distal periphery 115. In this variation, the peripheral element 155' is extended distally further than the embodiment of FIG. 3. In all other aspects, the components and feature of the variations of FIGS. 3 and 4 are the same. In FIG. 4, the tissue surface 156 is shown in phantom view as the distal periphery 115 is pressed into tissue and negative pressure NP in the interior channel 128 of the distal tip 105 provides negative NP' at the tissue surface 156 captured within the distal periphery 115. The negative pressure NP' then suctions the tissue surface 156 into contact with the surface 122 of the rolling member 120.

Referring to FIGS. 1 and 3, the applicator body 106 can have any suitable dimension about axis 108 and any shape suited for gripping with a human hand or fingers. Typically, the rolling member 120 can have a diameter ranging from 3 mm to 20 mm and often has a diameter ranging from 5 mm to 10 mm. Devices with rolling members 120 having a smaller diameter are suited for treating lips and larger rolling members are suited for treating facial skin or other skin surfaces. The components of the applicator 100 can be understood from FIGS. 1 and 3 and the body 105 is fabricated of a molded plastic, metal, a combination of plastic and metal or other suitable materials. The body 106 can be a combination of single-use or limited-use components together with non-disposable components. In a variation, the applicator body 106 can be a transparent or translucent plastic material which allows for viewing of the interior thereof during use.

Figure 5A:
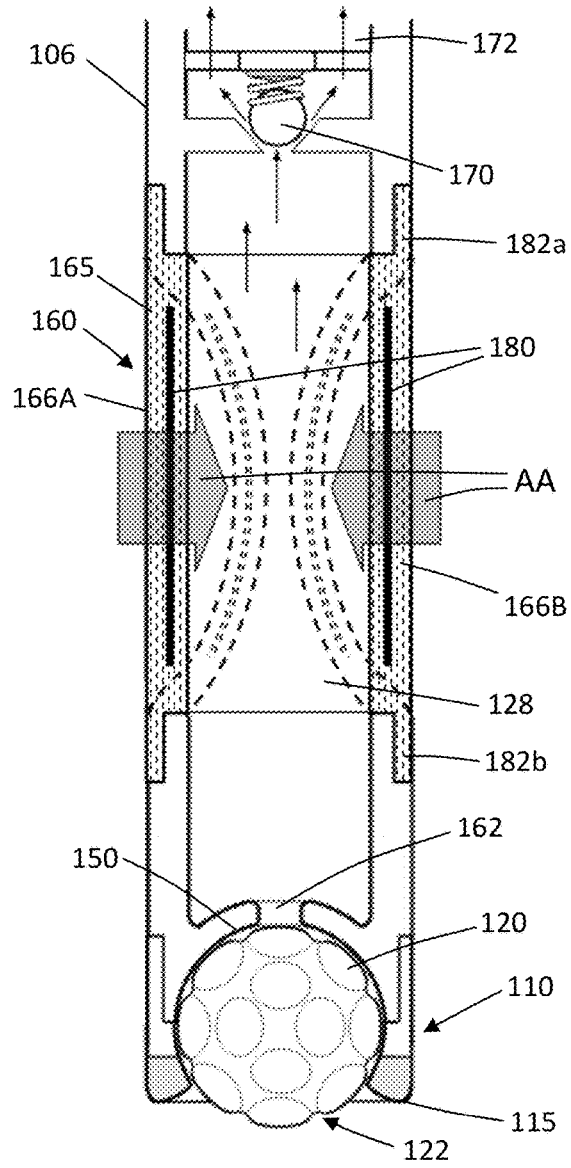
FIG. 5A is a sectional view of portion of the applicator body of the device of FIG. 1 showing a squeeze bulb component of the device in a first repose position, where the squeeze bulb is adapted to provide negative pressure in an interior channel of the device.
Figure 5B:
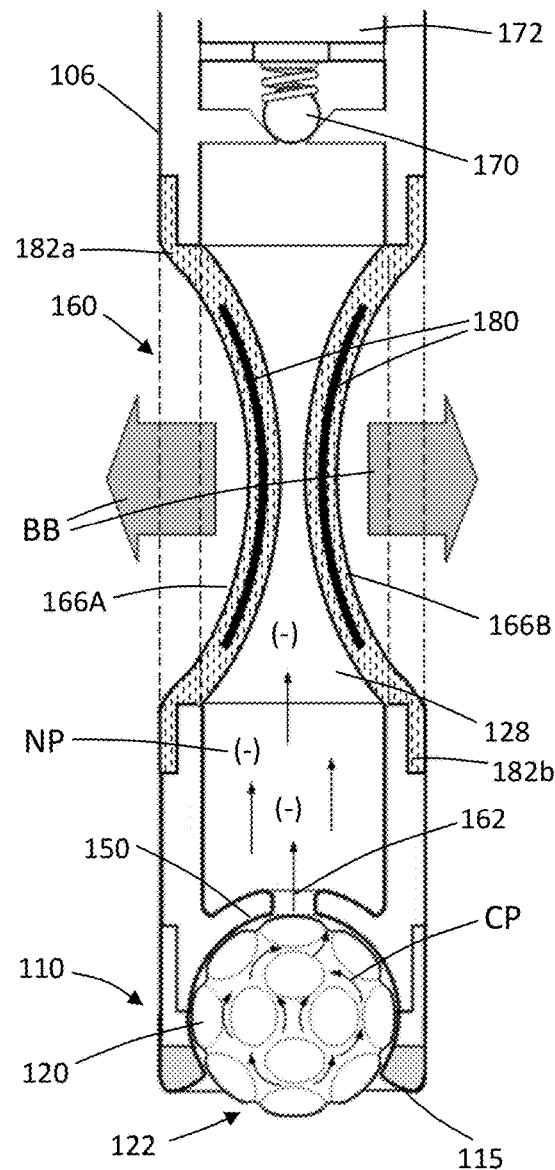
FIG. 5B is a sectional view of the applicator of FIG. 5A showing the squeeze bulb component in a second compressed and tensioned position, where the squeeze bulb when released from compression provides negative pressure in the interior channel of the device.
Figures 6, 7:
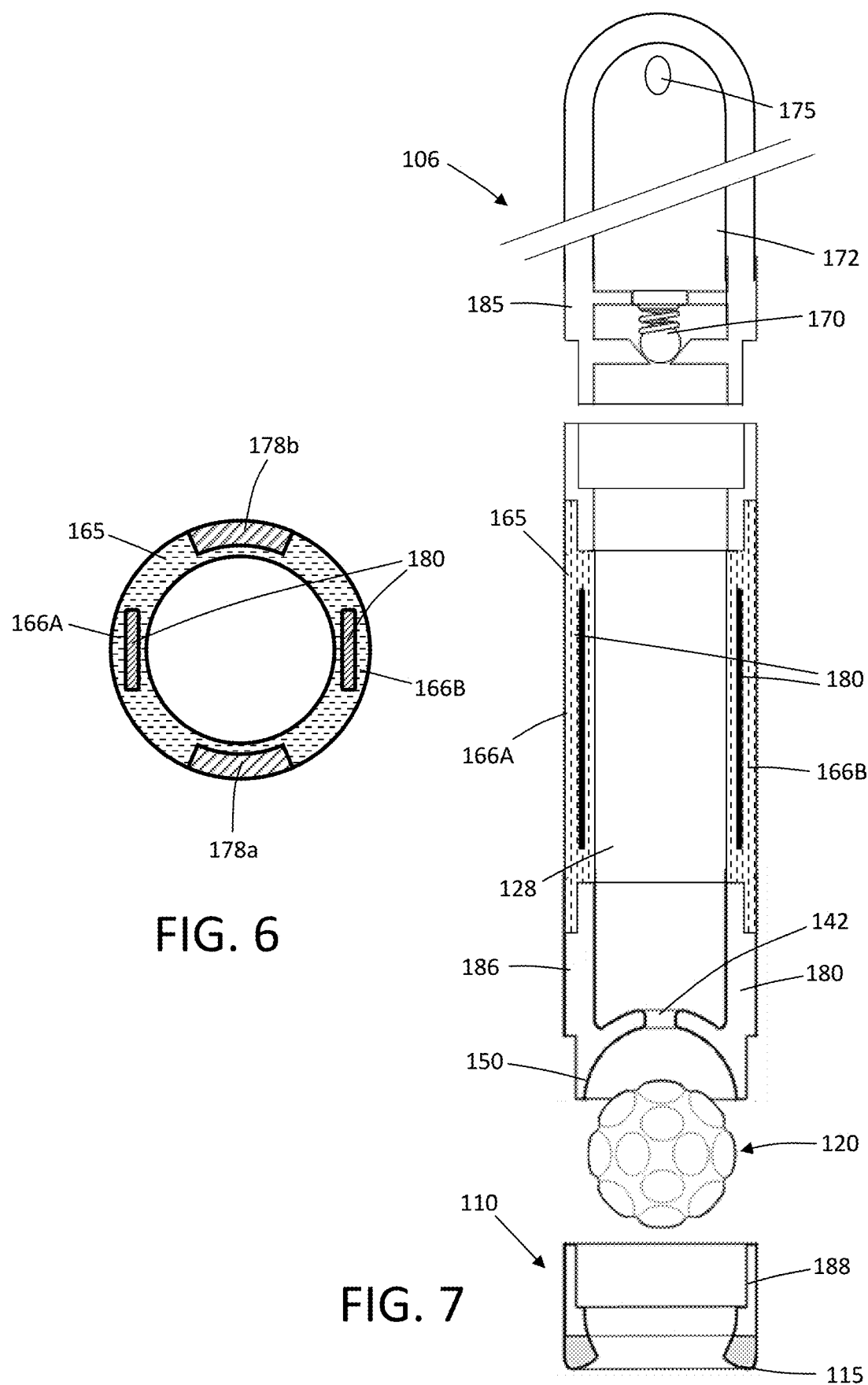
FIG. 6 is a sectional view of the applicator body taken along section 6-6 of FIG. 1.
FIG. 7 is an exploded view of the components of the device of FIG. 1 showing the various components de-mated from one another to allow for cleaning or replacement.

Referring now to FIGS. 1, 3 and 5A-5B, it can be seen that the applicator 100 includes a manually actuated negative pressure mechanism 160 in an interior aspiration chamber or channel 128 of the applicator 100 where the channel 128 has a distal end 162 that interfaces with the receiving space 150 around the rolling member 120 to apply negative pressure or suction around the rolling member 120 and to the targeted treatment site. In the device 100 as shown in FIGS. 1, 5A and 5B, the negative pressure mechanism 160 comprises an elastomeric squeeze bulb 165 where first and second sides 166A and 166B of the squeeze-bulb 165 are adapted to be pressed inwardly toward axis 108 which then causes air in the interior channel 128 to exit the channel 128 in the proximal direction through one-way valve 170 and thereafter through exit channel 172 in the proximal portion of the body to exit port 175 in the applicator body 106 (see FIGS. 1 and 7). As can be seen in FIGS. 1 and 6, the device body 106 has axial beam portions 178a and 178b that extend longitudinally as a support for the body 106 about the elastomeric squeeze bulb 165. In a variation, the squeeze bulb 165 has longitudinal leaf springs 180 molded into its elastomeric walls to urge the squeeze bulb 165 to the non-collapsed, linear shape as shown in FIGS. 1 and 5A. The proximal and distal ends (182a, 182b) of the elastomeric squeeze bulb 165 are bonded to the adjacent sections of the tubular body 106 to provide a sealed interior channel 128 (FIG. 5A).

In the variation shown in FIGS. 5A and 5B, a single leaf spring 180 is shown in each side of the squeeze bulb 165, but it should be appreciated that a plurality of spring elements can be used in each side 166A and 166B of the squeeze bulb. Alternatively, the spring elements may be disposed in the interior channel 128 and not fully embedded in the wall of the elastomeric squeeze bulb 165. In such an alternative, such leaf springs would then have a proximal and distal end that are fixed to the device body 106. It should be appreciated that other forms of spring elements may be used in a squeeze bulb structure such as collapsible-expandable braided structures, helical springs, zig-zag springs and the like. In a variation, the elastomer of the squeeze bulb 165 can be a transparent or translucent material to allow viewing of the interior thereof during use.

FIGS. 5A and 5B illustrate a method of operating the negative pressure mechanism 160. In FIG. 5A, the first and second sides 166A and 166B of squeeze-bulb 165 are pressed inwardly (see arrows AA) which tensions the elastomeric walls and springs 180 therein (phantom view in FIG. 2A) to displace the air in the interior channel 128. FIG. 5B then shows the squeeze bulb 165 in a tensioned, compressed shape which is being urged outwardly in direction of arrows BB that thereby creates negative pressure NP in the interior channel 128. The negative pressure NP in the interior channel 128 then communicates with the interface with receiving space 150 of rolling member 120. The negative pressure NP thus provides suction forces around the rolling member 120 to communicate with a surface of a treatment site engaged by applicator tip 110 and the exposed portion of the rolling member 120. In this variation, the negative pressure in interior channel 128 is created as air is pumped outwardly through channel 172 and exit port 175 faster than air flows inwardly around the rolling member, and negative pressure is maintained in interior channel 128 after the distal tip 110 is pressed against tissue and the negative pressure mechanism 160 is further actuated during use. In another variation described below, a normally closed finger-actuated valve is provided in the distal channel portion 162 to prevent air flow around the rolling member 120 to maintain negative pressure in the interior channel 128 after actuation of the negative pressure mechanism 160.

Now turning to FIG. 7, an exploded view of the device 100 of FIG. 1 illustrates that the components of applicator body 106 can be mated and de-mated to allow for cleaning or replacement of the component parts. In a variation, the body 106 has a first proximal body portion 185 that is separable from the central body portion 186 that carries the squeeze-bulb 165 to allow cleaning of the interior thereof. The proximal portion 185 of body 106 has the function of carrying the check valve or one-way valve 170 and a flow pathway 172 to exit port 175 and can comprise one or more elements that may be separable to allow for cleaning the interior thereof. In other variations, the one-way valve 170 can consist of a flap valve, a duck-bill valve, or any form of simple elastomeric check valve. Such a one-way valve can be disposed either in the interior of the body as in FIG. 7 or the valve can be disposed at the proximal end of the device and comprise a feature of the exit port 175. As can be seen in FIG. 7. the first central body portion 186 can be de-coupled from the distal body portion 188 to allow cleaning thereof and cleaning or replacement of the roller member 120. The various components are shown in FIG. 7 with cylindrical mating features having a suitable slip fit that may be adequate to maintain negative pressure in interior channel 128 and other components of the device. In another variation, the mating connections may be provided with o-rings to enhance sealing between the components. In FIG. 7, the body portions 186 and 188 separate axially but any other form of structure can be used in a side-to-side or other arrangement to allow assembly of the members to provide the spherical receiving space 150 for receiving and capturing the rolling member 120.

Figure 8D:
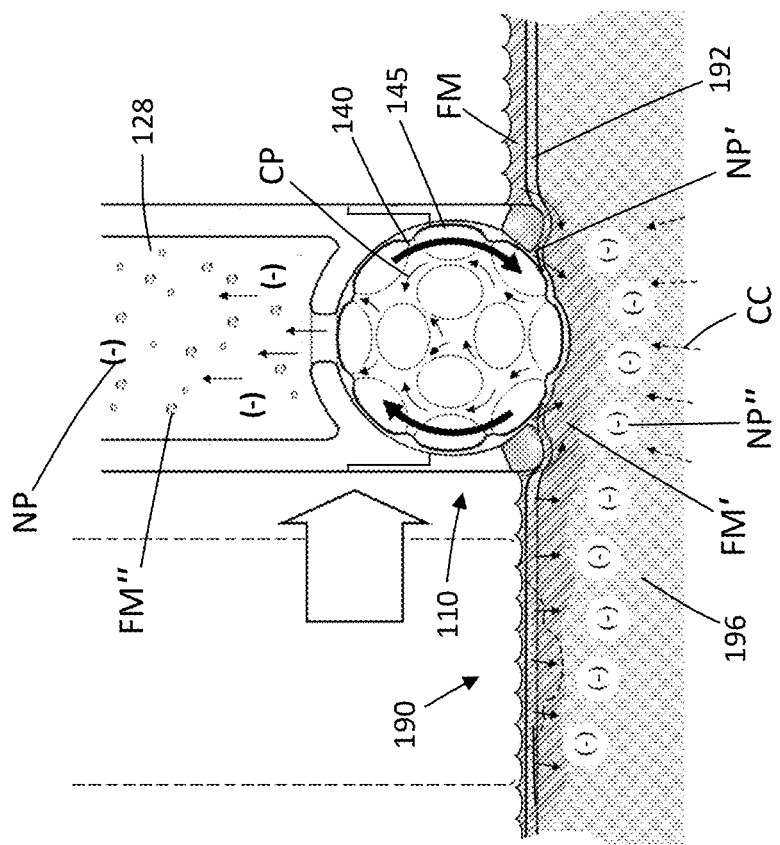
FIG. 8D illustrates a subsequent step where the applicator tip is translated across the tissue surface which continues to apply negative pressure about the rolling member that causes negative pressure in subsurface tissues which in turn causes absorption and penetration of the treatment media into the tissue.

FIG. 8A through 8D illustrate a method of using the device 100 of FIGS. 1, 3 and 5A-5B to treat a subject's lips 190. In FIG. 8A, the subject has topically applied flowable treatment media FM to the treatment site. It should be appreciated that the flowable or fluid media FM can consist of a liquid, gel or flowable media that can contain medications, serums, nourishing agents, botanicals, plumping agents, vitamins, colorings, cosmetics, peeling agents, desensitizers, hormones and any other flowable media known in the art for topical use. The operator of the applicator 100 then actuates the sides 166A and 166B of the squeeze bulb 165 (indicated by arrows AA) to thereby create negative pressure NP in the interior channel 128 of the device. FIG. 8B is an enlarged schematic view of the applicator tip 110 and rolling member 120 as in FIG. 8A just prior to being pressed into contact with the subject's lips 190 where the fluid media FM is shown on the tissue surface 156. In FIG. 6B, it can be seen that a negative pressure NP is provided in the interior channel 128 that communicates with the receiving space 150 around the spherical rolling member 120.

Figure 8C:
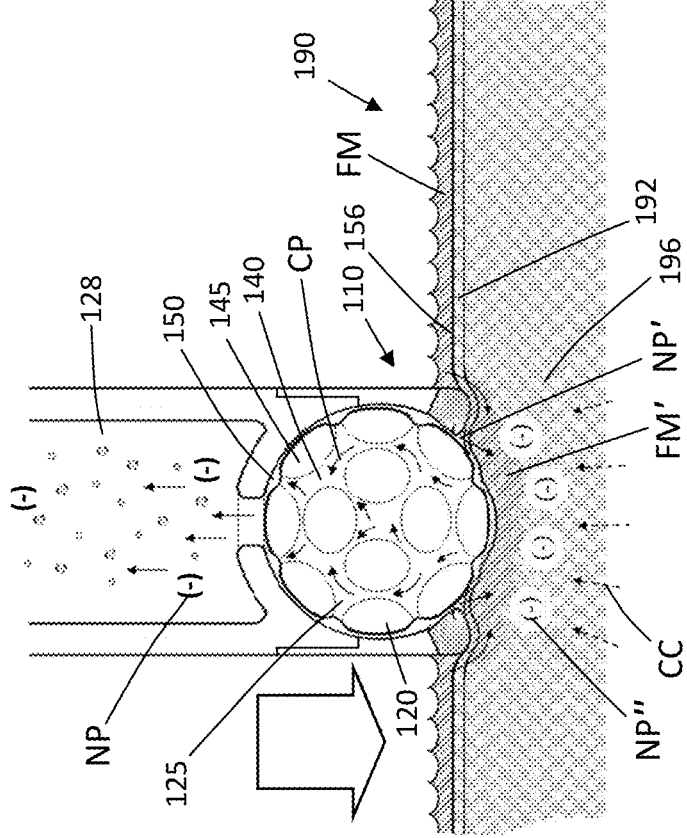
FIG. 8C illustrates a subsequent step of the method where applicator tip is pressed into contact with the tissue surface which applies negative pressure about the rolling member and to the tissue surface as well as causing negative pressure within subsurface tissue to further cause absorption of the treatment media.

FIG. 8C illustrates a subsequent step of the method wherein the distal periphery 115 of the applicator body 106 and rolling member 120 are pressed into the tissue surface 156 and where negative pressure NP in the interior channel 128 communicates with the receiving space 150 and discontinuities 125 in the surface of the rolling member 120 to cause negative pressure NP' at the tissue surface 156. The irregularities of recessed portions 140 and projecting portions 145 in the roller surface 122 (see FIG. 3) causes the surface layer 156 of the tissue to be stretched, indented and tensioned (i.e., manipulated) as well as being exposed to negative pressure NP'. This negative pressure NP' at the tissue surface 156 can cause a transient negative pressure NP'" to migrate through the surface tissue layer 192 to a subsurface tissue region 196 which will cause upward migration of intracellular fluids towards the tissue surface 156 as indicated by arrows CC (and potentially a bruise as capillaries may be damaged). The negative pressure NP'" in subsurface tissue 196 more importantly further causes fluid media FM at the tissue surface 156 about the spherical rolling member 120 to penetrate inwardly toward the negative pressure NP'" in the subsurface tissue 196. Thus, the subsurface negative pressure NP'" causes absorbed fluid media indicated at FM' in FIG. 6C. Further, the circuitous path CP of the fluid media FM within the discontinuities 125 (see FIG. 3) of the spherical rolling member 120 causes the fluid media FM to migrate over the tissue surface 156 to maintain fluid contact with the manipulated or affected (i.e., stretched, penetrated) tissue. All of these effects cause the fluid media FM to the absorbed by, and penetrate into, subsurface tissue 196 indicated at FM'.

FIG. 8D shows the applicator tip 110, distal periphery 115 and rolling member 120 being translated across the tissue surface 156 which rolls the rolling member 120 and transiently creates negative pressure NP'" over a larger expanse of subsurface tissue 196 to cause absorption of fluid media FM' over the treated region. At the same time, small amounts of the fluid media FM'' are aspirated into the interior channel 128 in response to negative pressure NP therein.

In general, a method of the invention for treating a subject's skin or lips comprises contacting a tissue surface with a rolling member carried at a distal end of an applicator body, moving the rolling member over the tissue surface and creating negative pressure about the rolling member in contact with the tissue surface to transiently cause negative pressure in subsurface tissue to enhance permeability of the tissue surface. Typically, the treatment media is applied topically to the subject's skin or lips before use of the negative pressure applicator. During use, the translation of the applicator tip over a tissue surface causes the surface discontinuities of the rolling member to compress, stretch, tension and/or pierce the tissue surface to enhance penetration or absorption of the treatment media.

As a negative pressure in the interior channel 128 of the device is reduced during use, the operator can intermittently or continuously actuate the squeeze bulb 165 to increase or maintain negative pressure NP in the interior channel 128 while translating the applicator tip 110 and rolling member 120 across the tissue surface 156. All of these effects combine to enhance fluid absorption and penetration. Following use, the operator can disassemble the device 100 as shown in the exploded view of FIG. 7 and clean the interior channel 128 and other components for example with running water. The device components then may be reassembled for future use.

The variation of FIGS. 1, 3, 5A and 5B illustrate the squeeze bulb 165 as a form of pump that is suitable for creating negative pressure in interior channel 128 of the applicator 100, but it should be appreciated that any type of manually-actuated pump may be used and fall within the scope of the invention. Typically, a positive displacement pump is suitable which can be a piston pump, a syringe pump, bellows pumps, a peristaltic pump, a gear pump, an impeller pump, a vane pump or a diaphragm pump.

FIG. 9 illustrates a distal applicator tip 205 of another variation of an applicator that is otherwise similar to that of FIGS. 1 and 3. In FIG. 9, the rolling member 120' is similar to that of FIG. 3 with similar projecting portions 145. In this variation, the recessed portions 140' have an abrasive surface 210 which, for example, can be diamond dust adhered thereto or sharp abrasive edges molded into a plastic rolling member. The abrasive surface 210 provides for traction between the rolling member 120' and the skin surface 156 as well causing micro-penetrations into the skin surface 156 as a form of tissue manipulation to thereby enhance penetration of fluid treatment media into the skin as described previously. In this variation, the distal periphery 115' is shown to extend distally compared to that of FIG. 3 such that the surface 122' of the rolling member 120' does not extend beyond the distal periphery 115'. In such an embodiment, where the rolling member surface 122' is somewhat recessed in the tip 205, it is useful to provide increased traction between the rolling member 120' and a skin surface. As can be understood in FIG. 9, the abrasive surface 210 is recessed relative to the outermost surfaces of the projecting portions 145 so that the rolling member 120' rolls smoothly in the receiving space 150.

FIG. 10 illustrates another variation of distal applicator tip 215 that is similar to previous embodiments except the rolling member 220 has projecting portions 225 surrounded by a recessed region 240 that carries a plurality of sharp elements that can be micro-needles 244 or molded sharp points that provide for traction between the rolling member 220 and the tissue surface 156 as well for penetrating the skin surface 156 as a form of tissue manipulation to thereby enhance penetration of fluid media into the skin. In FIG. 10, a limited number of micro-needles 244 are shown, but the number may range from dozens to many hundreds of such micro-needles. In the variation of FIG. 10, the distal peripheral element 255 that surrounds the exposed portion of the rolling member 220 is shown of a resilient elastomeric material with an annular void 256 therein to allow the element is to be flexed and compressed when in contact with tissue to create an effective seal. The distal end 258 of the housing is configured to prevent the peripheral element 255 from being flexed into contact with the rolling member 220.

Figure 11:
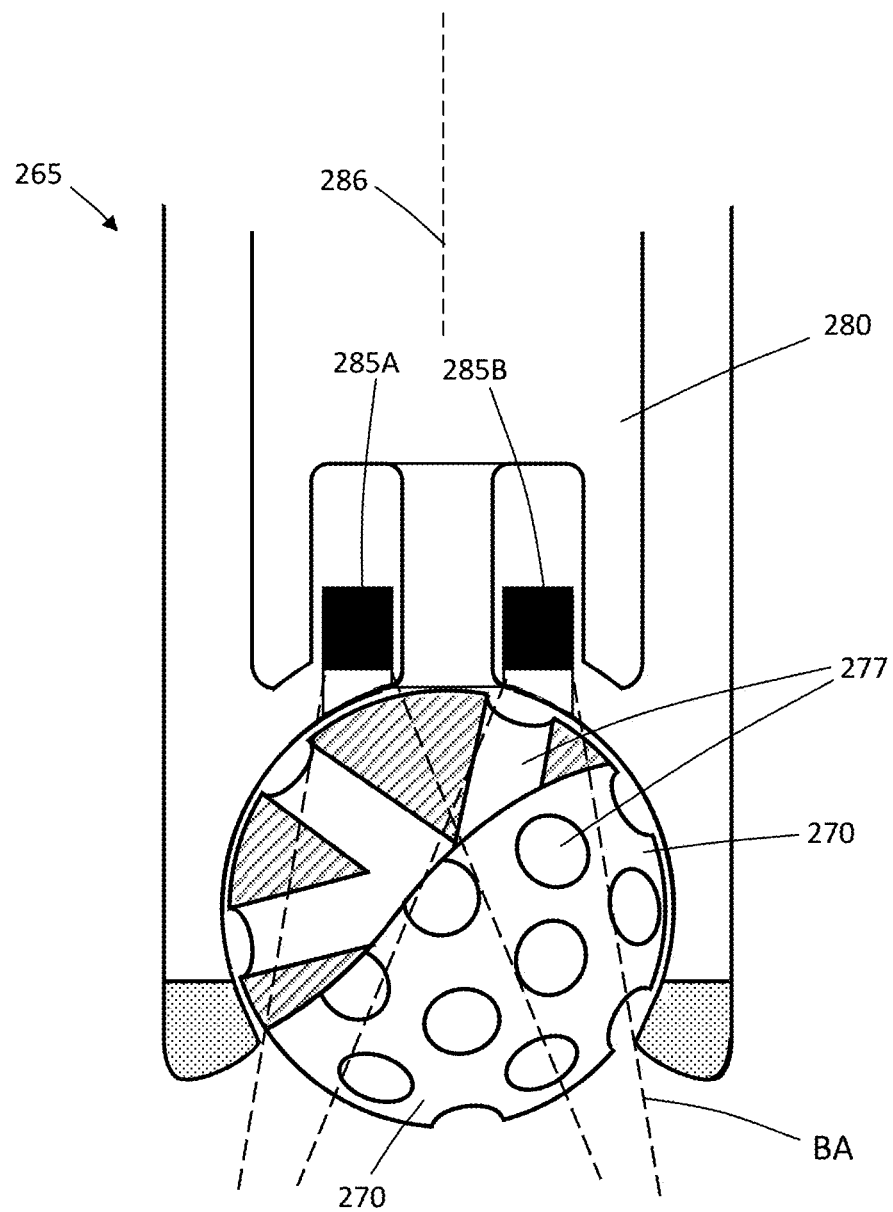
FIG. 11 is a cut-away view of another variation of applicator tip similar to that of FIG. 1 where the distal housing carries LEDs for applying light energy to tissue.

FIG. 11 illustrates another variation of distal applicator tip 265 that has a rolling member 270 with outer surface portion 275 and through-channels or bores 277 that function as means for communicating a negative pressure NP in interior channel 280 with tissue in contact with the rolling member 270. The number of bores 277 can range in number from 10 to 100 or more and can be any suitable dimension ranging from 1% of the diameter of the rolling member to 20% of the diameter or rolling member 270. FIG. 11 also illustrates another feature in this variation of applicator tip 265 that comprises at least one LED and in this variation is shown as two LEDs 285A and 285B that emit at least one wavelength of light for treating tissue. In this variation, the rolling member is formed of a transparent material such as a plastic or glass to permit light transmission therethrough. The LED beam angle BA is shown in FIG. 11 and can range from 15° to 60°. In a variation (not shown), the rolling member 270 can carry embedded or surface light shaping diffusers that comprise micro-structures randomly or controllably positioned on or within the rolling member 270 to modify the LED light beam by changing the direction of its energy. Such light shaping diffusers can shape the light beam(s) to propagate laterally relative to the axis 286 of the applicator tip 265 to broadly treat tissue in contact with the rolling member 270. In the variation of FIG. 11, the LEDs 285A and 285B can emit a red-light wavelength which research indicates can penetrate deep into skin and stimulate the mitochondria, which has an anti-inflammatory and rejuvenating effect. Such red-light therapy has been found to accelerates skin repair, regulate oil production and improve circulation, and is known as a medically-approved treatment for rosacea. The LEDs also can emit blue light which has antibacterial properties for the treatment of acne, eczema and psoriasis. Other wavelengths also can be used and fall within the scope of the invention. The LEDs 285A and 285B can be coupled to a re-chargeable battery (not shown) carried by the applicator.

Figure 12:
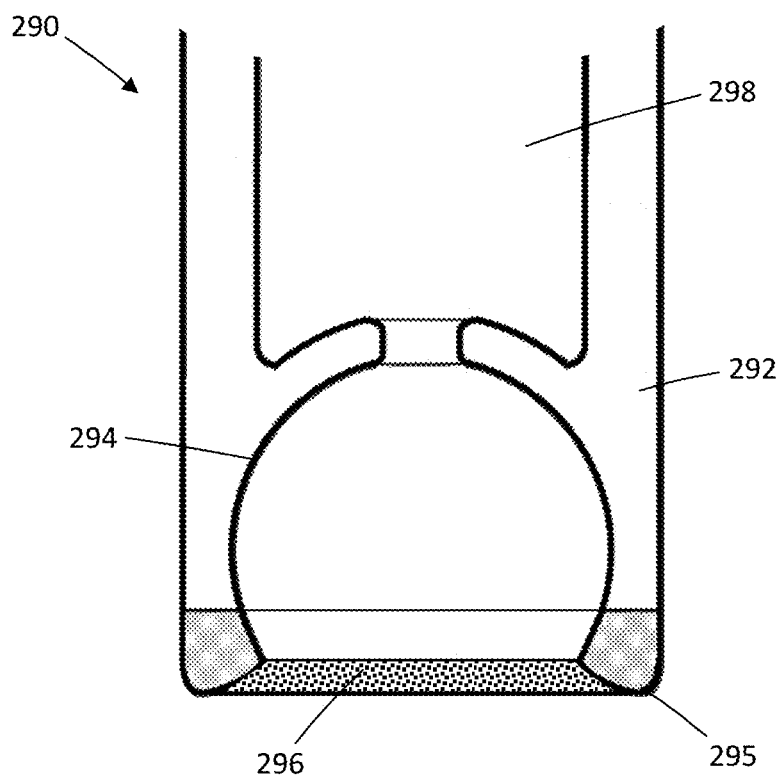
FIG. 12 is a sectional view of another variation of roller housing that is configured with an abrasive surface around a distal periphery of the applicator body for providing a dermabrasion effect to enhance fluid penetration into a skin surface.

FIG. 12 illustrates a variation of an applicator body 290 with a distal housing portion 292 with a receiving space 294 for receiving a rolling member (not shown), where the rolling member can be similar to any previously described embodiments. In this variation, the distal periphery 295 is configured with a portion having an abrasive surface 296 that can consist of abrasive particles such as diamond dust adhered to the distal periphery 295. Alternatively, the abrasive surface 296 can consist of sharp edges and features formed in a molded, machined, printed or etched material that comprises the distal periphery 295. The abrasive surface 296 functions to abrade and remove a skin surface layer as the distal housing 292 and periphery 295 is translated over a tissue surface. Such an abrasive effect enhance fluid penetration into and through the surface tissue layer. In all other aspects, the rolling member and negative pressure in the interior channel function 298 as described previously to perform methods of the invention.

Figure 13:
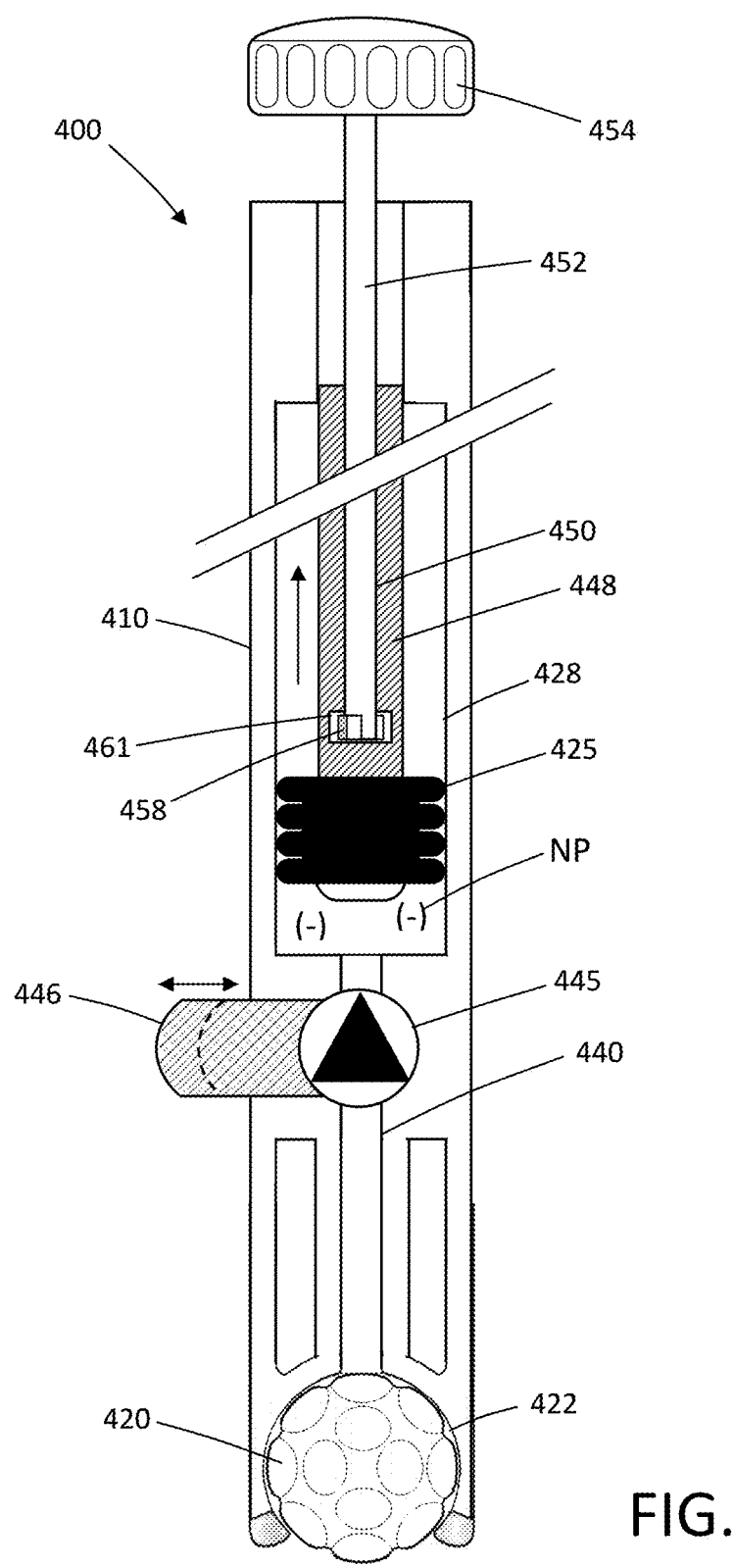
FIG. 13 is a sectional view of another variation of a negative pressure treatment device where negative pressure is created by a syringe-type piston mechanism, and where the applicator further includes a finger-actuated valve for releasing aspiration forces to treat tissue.

FIG. 13 illustrates another variation of a treatment device 400 that is similar to that of FIGS. 1, 3 and 4 except that a different negative pressure mechanism 405 is provided in the applicator body 410. In the variation of FIG. 13, the rolling member 420 and the receiving space 422 are the same as described previously. The variation of FIG. 13 is adapted to create negative pressure NP with a syringe-type piston 425 that is movable in an interior syringe chamber 428 to provide negative pressure NP therein. The manually actuated piston 425 and chamber 428 communicate with a flow channel 440 that interfaces with rolling member 420 as described previously. In this variation, a finger-actuated valve 445 with actuator button 446 that has a normally closed position is provided in the flow channel 440 intermediate the syringe chamber 428 and the rolling member 420. In use, the negative pressure NP can be maintained in the syringe chamber 428 until the operator actuates the valve 445 apply negative pressure or suction forces to an engaged tissue surface. In one variation, the piston 425 is coupled to an actuator shaft 448 that is moved axially in the proximal direction to create negative pressure NP in the syringe chamber 428. The actuator shaft 448 is shown in FIG. 13 as a tubular member with a bore 450 therein that receives a telescoping member 452 with grip 454. The telescoping member 452 has distal tabs 458 that can be rotated in an offset 460 in bore 450 to engage and disengage the shaft 448 to thus provide an axially collapsible shaft assembly.

Figure 14:
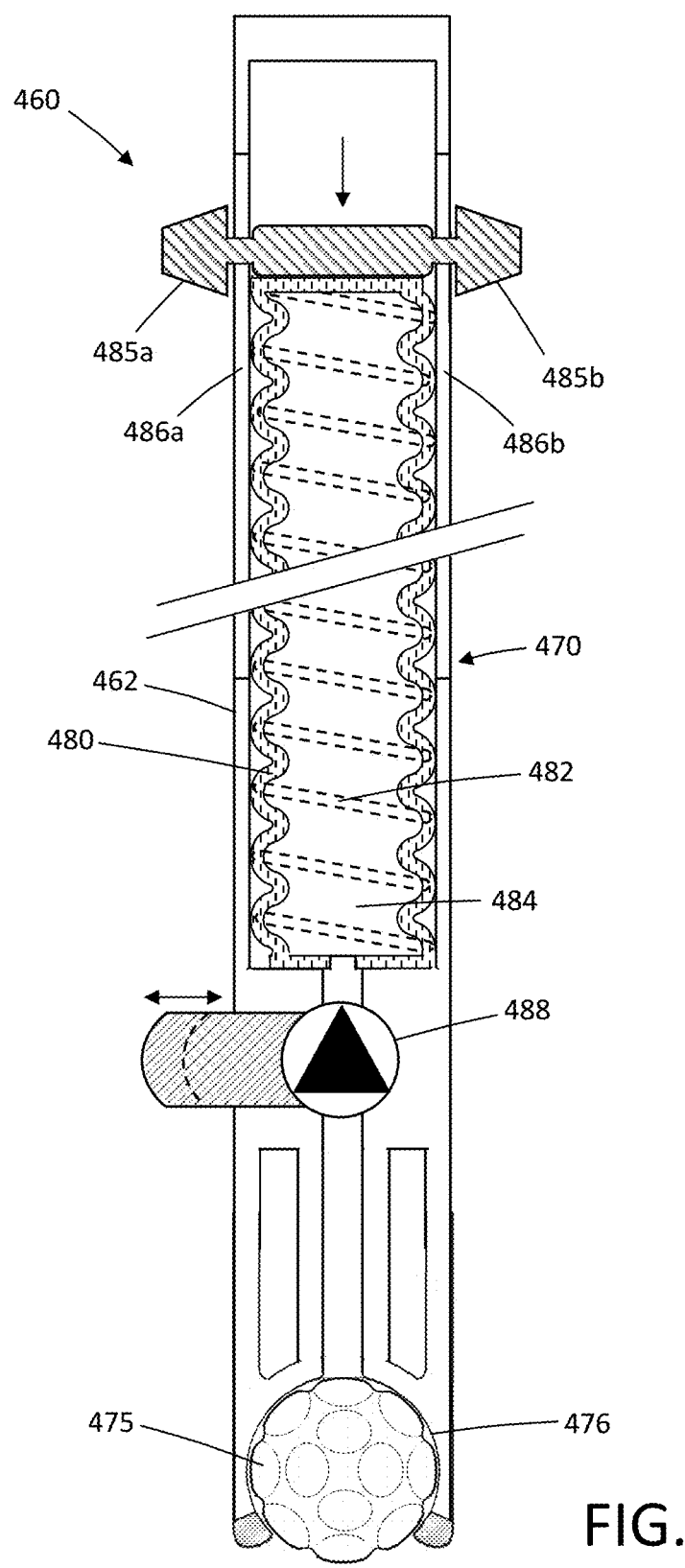
FIG. 14 is a sectional view of yet another variation of a negative pressure treatment device where negative pressure is created by a manually-actuated bladder or bellow mechanism.

FIG. 14 illustrates another variation of a treatment device 460 with an applicator body 462 that is similar the previous embodiment of FIG. 13 except that it provides a different negative pressure mechanism 470. In the variation of FIG. 14, the rolling member 475 and receiving space 476 are the same as described above. In the variation of FIG. 14, negative pressure is provided by a bladder or bellows 480 that is urged toward an expanded shape by a strong helical spring 482 to create negative pressure in an interior chamber 484 thereof. The bladder 480 is collapsible by finger-actuated tabs 485a and 485b that extend through slots 486a and 486b in the applicator body 462. A finger-actuated valve 488 is provided as in the previous embodiment, where the valve is held in an open position as the bladder 480 is actuated to the collapsed position. In all other aspects, the method of using the device 250 of FIG. 8 is the same as described above.

Figures 15, 16:
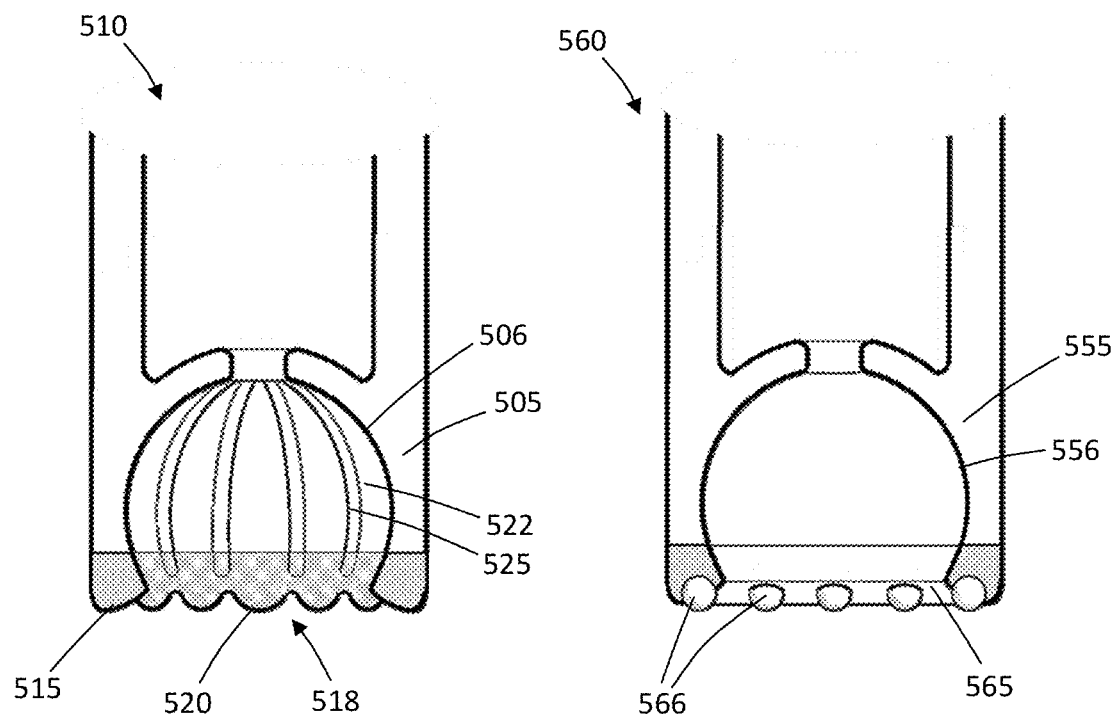
FIG. 15 is a sectional view of another variation of roller housing that is configured with an undulating distal periphery for manipulating tissue.
FIG. 16 is a sectional view of another distal roller housing that is configured with a distal periphery carrying a plurality of rollers for reducing friction with a tissue surface during use and for manipulating tissue.

FIG. 15 illustrates another variation of a distal housing 505 and receiving space 506 of an applicator body 510 shown without a rolling member, where the rolling member can be similar to the previous embodiment of FIGS. 1 and 3 or other embodiments. In this variation, the distal periphery 515 is formed with a series of undulations 518 that are adapted to manipulate a tissue surface similar to the irregular surface of a rolling member. Thus, as the distal housing 505 is translated over a tissue surface, the projecting portions 520 of the undulations will indent, tension and stretch surface tissue which can enhance fluid penetration into and through the surface tissue layer. FIG. 15 also shows that the spherical inner surface 522 of the roller receiving space 506 has surface discontinuities or grooves 525 therein that provide a flow path for negative pressure NP in channel around the rolling member. Thus, there can features in either or both the surface of the rolling member and the surface of the receiving space 522 that provide flow pathways for negative pressure NP to perform the method of the invention. In this variation, it should be a appreciated that a rolling member (not shown) could have an entirely spherical abrasive surface and rotate smoothly in the receiving space 506 since the number of apices of abrasive elements would number in the thousands and the flow pathway for negative pressure to the tissue surface would be provide largely or entirely by the surface discontinuities or grooves 525 and partly by the interstices between the projecting portions of the abrasive elements.

FIG. 16 illustrates another variation of a distal housing 555 and receiving space 556 of an applicator body 560 where the distal periphery 565 of the housing 555 carries a plurality of roller balls 566 which project slightly from the distal periphery 565. Such roller balls 566 can serve the function of manipulating tissue as described above while the same time reducing friction of the distal housing 555 with the tissue surface as it is translated over a tissue surface.

Figure 17:
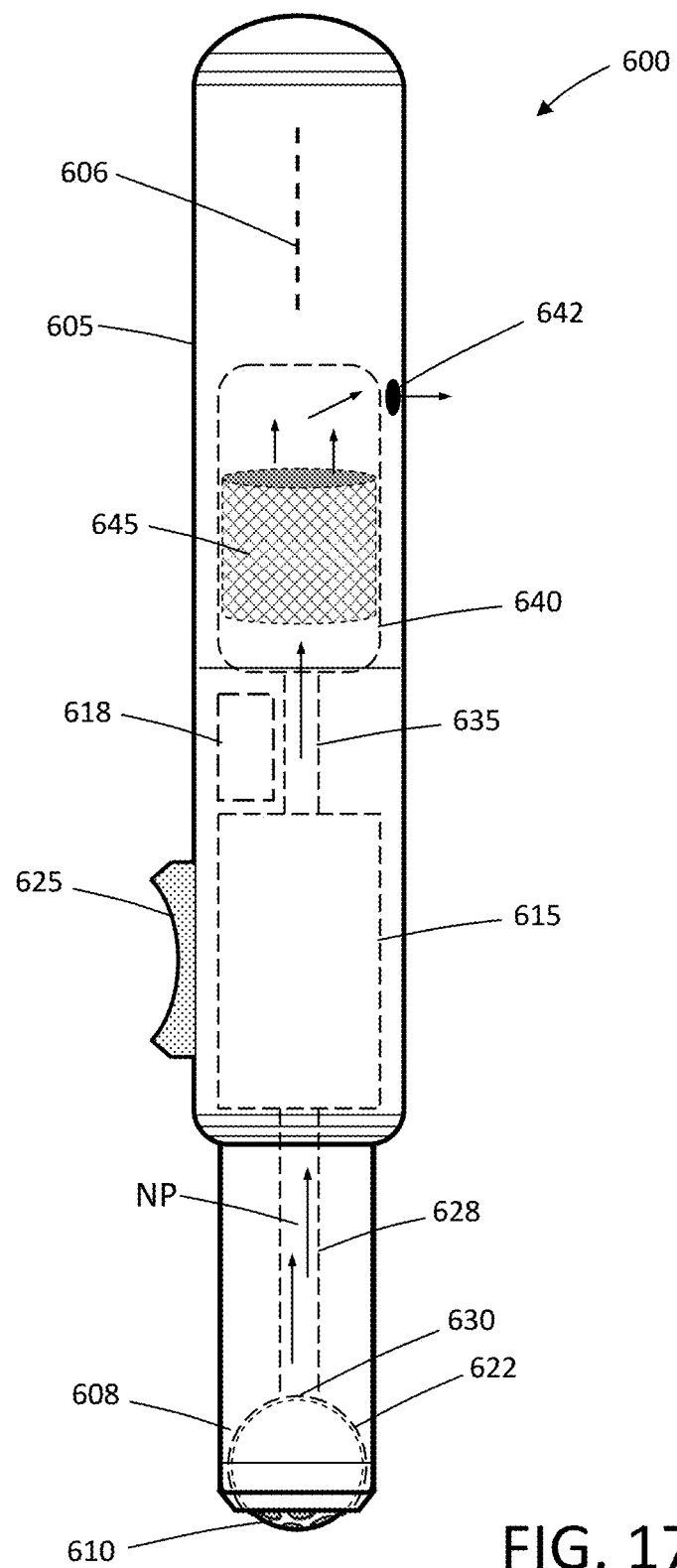
FIG. 17 is an elevational view of another variation of skin treatment device or applicator with a distal rolling member and a DC motor driven pump assembly with filter carried in the applicator body.

FIG. 17 illustrates another variation of a treatment device 600 that is similar to that of FIGS. 1, 3 and 4 with an elongate body 605 extending about longitudinal axis 606 and is configured with a distal housing 608 that carries a rolling member 610. In this variation, the negative pressure mechanism comprises a pump assembly 615 that comprises a pump and DC motor powered by a battery 618, both of which are carried in the applicator body 605. This variation again is adapted for use with a topically applied treatment media as described previously. In the variation of FIG. 17, the rolling member 610 is rotatable in any direction in the receiving space 622 of the distal housing 608 and is similar to previous variations. The pump assembly 615 can comprise any suitable form of pump, and in a variation is a diaphragm pump coupled to a 3.7 W DC motor that is operated by rocker switch 625 in the applicator body 605. In one variation, the rocker switch 625 is adapted to select between one or more settings of negative pressure, for example, up to 63 kPa (9.14 psi). The variation of FIG. 17 is adapted to create negative pressure NP in the distal aspiration or extraction channel 628 that interfaces with rolling member 610 about an open termination 630 of the said aspiration channel 628. Thus, the pump assembly 615 aspirates air and fluid droplets through or around the rolling member 610 and through the pump assembly 615 into the proximal aspiration or extraction channel 635, which can include an interior chamber 640, in the applicator body 605. At least one vent or aperture 642 is provided for exhausting flow media air from extraction channel 635 and chamber 640. As can be seen in FIG. 17, the interior chamber 640 carries a filter 645 for capturing liquid droplets of the aspirated treatment media. In all other aspects, the variation of FIG. 17 functions as previous variations to enhance fluid penetration into a subject's skin, and the rolling member 610 can consist of any of the various types described above. While this variation shows that pump assembly 615 is powered by a battery 618, it should be appreciated that a power cord and a remote power source also fall within the scope of the invention. Further, in the variation shown in FIG. 17 that uses a battery 618, the applicator body 605 can be configured with electrical contacts in a surface of the body 605 to cooperate with a charging stand as is commonly known in the field of battery-operated handheld devices. As in previous variations, the applicator body 605 can consist of several mating components that can be disassembled to allow cleaning of the interior components of the device including the rolling member 610, the receiving space 622, the pump assembly 615, the distal aspiration channel 628, the proximal aspiration channel 635, chamber 640 and the filter 645.

Figure 18:
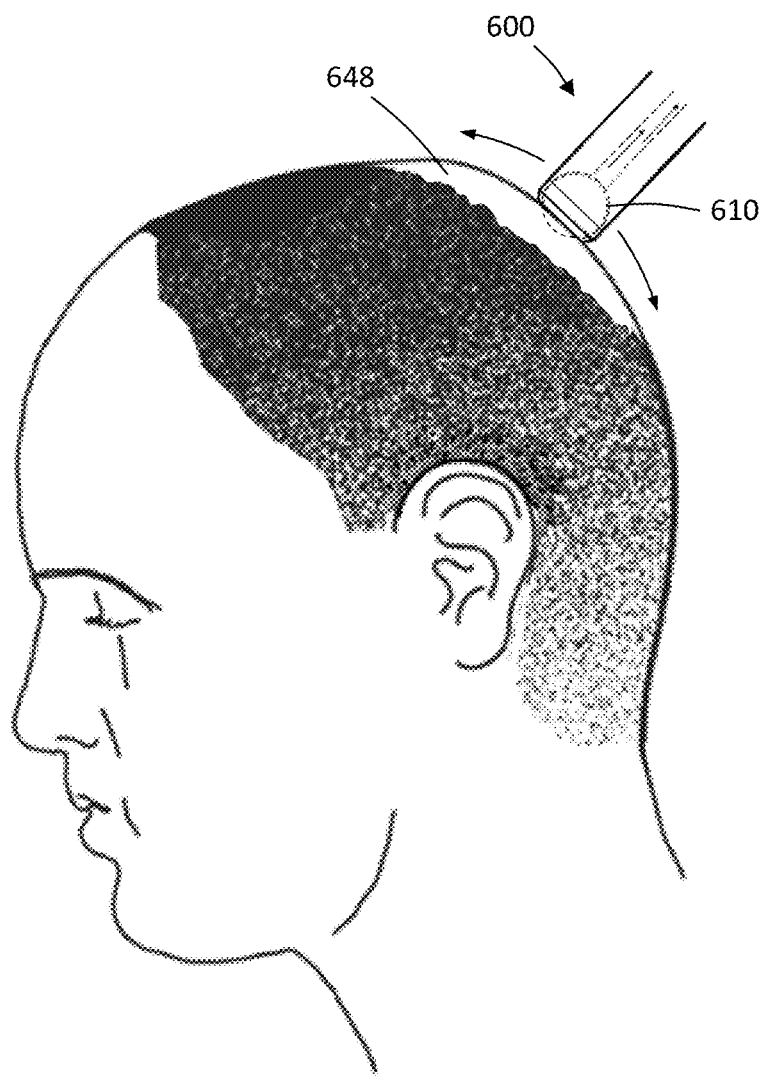
FIG. 18 is an illustration of a method of treating hair loss using the applicator of FIG. 17 to apply and deliver pharmacologic agents to a treatment site on a patient's scalp.
Figure 21:
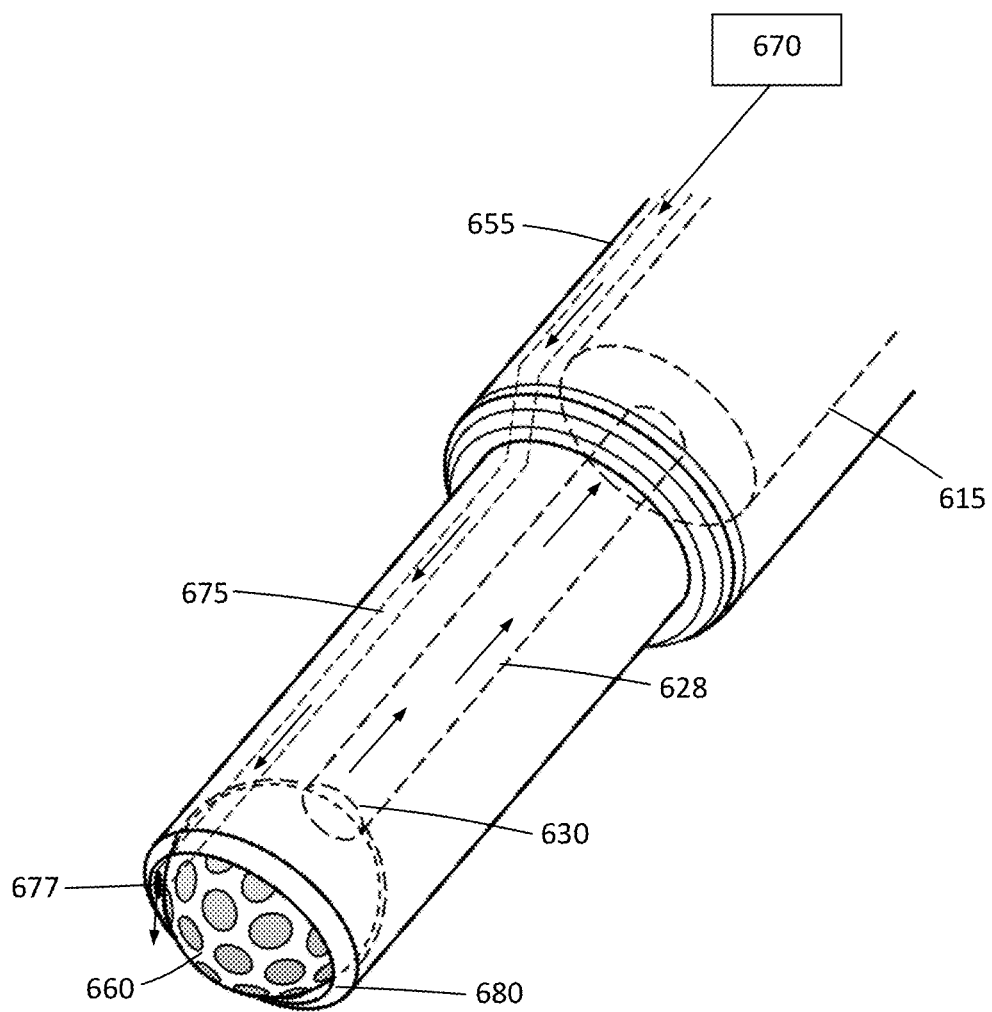
FIG. 21 is an enlarged perspective view of the distal portion of the applicator of FIG. 19.

The device of FIG. 17 is adapted for use in the methods of delivering or applying fluid to tissue as described previously. In another method, the applicator 600 of FIG. 17 can be used to treat hair loss as shown in FIG. 18. It can be appreciated that the applicators described above, including that the applicator of FIG. 17, include an internal pump assembly 615 and are designed to enhance penetration of fluid treatment media into subsurface tissue under a targeted site of the subject's skin. In FIG. 18, the applicator or treatment device 600 is shown being used to apply and enhance the penetration of treatment media into the skin of a subject's scalp 648. In this method, the treatment media can include at least one of finasteride, minoxidil, dutasteride and a corticosteroid. Currently, such pharmacologic agents have been applied topically and have shown to have an effect in the restoration of hair growth. The applicator 600 of FIG. 17 and the applicator 650 shown in FIGS. 19-21 are thus adapted to enhance the penetration of such agents into subsurface tissue below the skin surface to enhance hair growth. In other variations, the treatment media can include a psoralen and the applicator body can include LEDs with the appropriate wavelength to interact with the psoralen to stimulate hair growth. Currently, psoralens has been investigated for enhancing hair growth when irradiated with selected light wavelengths, for example UV wavelengths.

In general, a method for treating a subject's hair loss comprises topically applying a hair growth treatment media to targeted tissue of a subject, contacting the tissue and treatment media with an applicator and causing negative pressure about the applicator in contact with the tissue to transiently cause negative pressure in subsurface tissue to enhance penetration of the treatment media into the subsurface tissue. Further, the method can move the applicator over the tissue to treat broad areas of the subject's scalp. In such a treatment, the treatment media includes at least one finasteride, minoxidil, dutasteride, nanoxidil, redensyl, capixyl, procapil and/or other agents that inhibit DHT production which are known in the field to assist in hair growth. Additionally, a corticosteroid and a psoralen may be used. The step of causing negative pressure includes actuating a vacuum pump mechanism in the applicator body, or alternatively, the negative pressure source is remote form the applicator and coupled to the applicator with a flexible tubing. In one variation, the negative pressure is pulsed to allow manipulation and relaxation of the tissue surface to enhance fluid penetration. In another variation similar to previous applicators, the negative pressure is provided at the interface of the subject's skin by a rolling member 610 in the applicator tip which provides a flow path through and/or around the rolling member 610 (see FIG. 17). As described in previous variations, moving the rolling member 610 manipulates tissue to thereby enhance penetration of the treatment media into subsurface tissue. Such tissue manipulation can consist of compressing, stretching, tensioning and/or piercing the tissue surface using the surface features of the rolling member 610. In a variation, the rolling member 610 further removes or exfoliates the epidermis with surface features of the rolling member to thereby enhance penetration of the treatment media in the targeted tissue. The applicator body of FIG. 17 can further be provided with the source of treatment media in a cartridge or reservoir carried by the applicator body as will described next in the variation of FIGS. 19-21. The method of treating hair loss described above also can be performed with any of the treatment devices of FIGS. 22-29 that provide negative pressure and tissue manipulation as well as the treatment device of FIGS. 29-30 that provides negative pressure and manipulates tissue without a rolling member.

Figure 23:
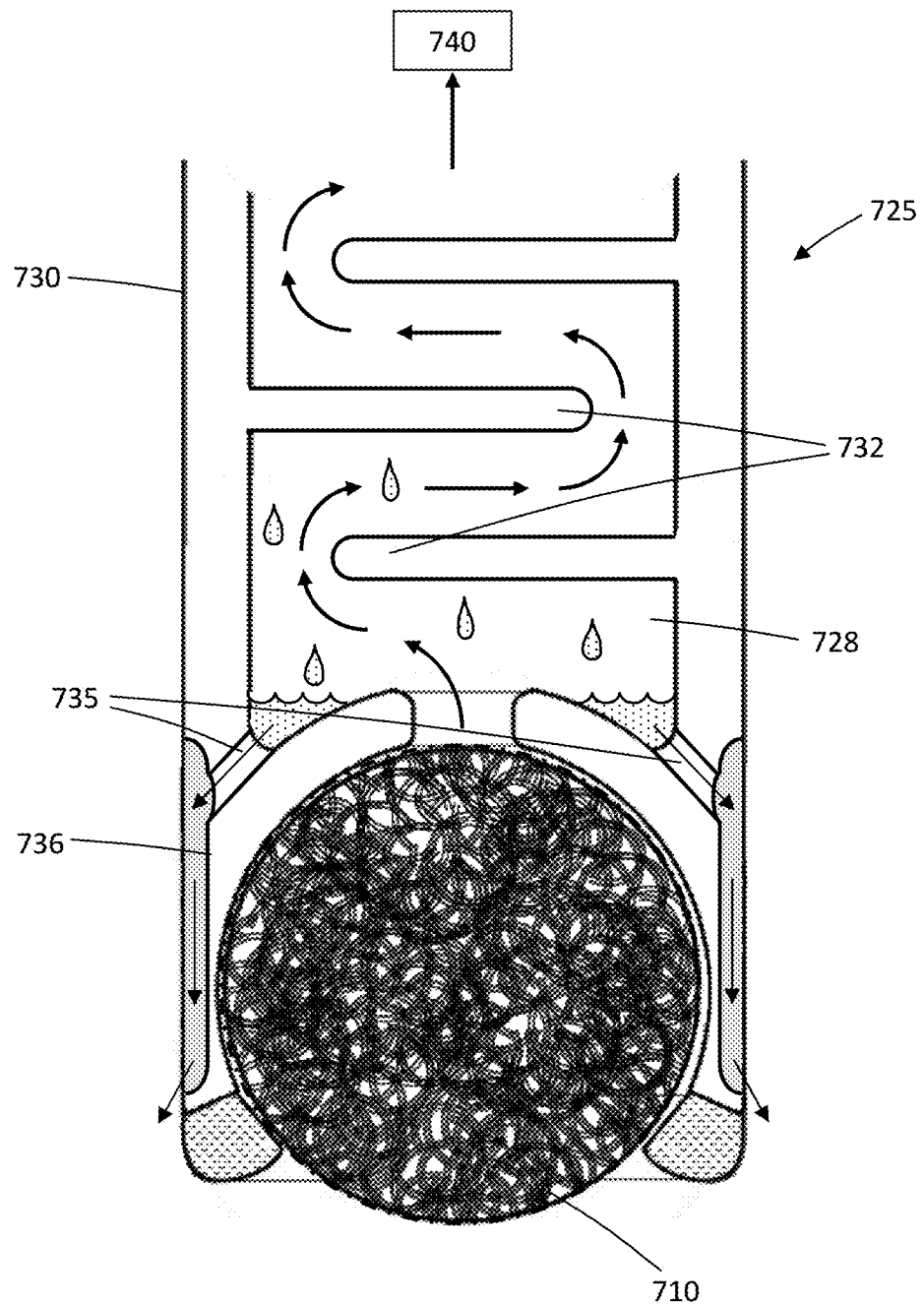
FIG. 23 is a section view of a distal portion of another variation of an applicator that includes baffles in an outflow channel to capture liquid droplets from outflows.

Now turning to FIG. 19-21, another variation of applicator 650 is shown that includes an elongated applicator body 655 with a distal rolling member 660 as described previously. In this variation, the applicator body 655 again carries a pump assembly 615 and battery 618 operated by a switch 625 with fluid and water droplets being extracted through the distal channel 628 and pump assembly 615 to a proximal chamber 640 carrying a filter 645 as described previously. In the embodiment of FIG. 19, the applicator 655 carries a fluid reservoir 670 that may be detachable or non-detachable and is adapted to carry the treatment fluid TF. FIG. 19 shows the applicator body 655 with the various components in phantom view and FIG. 20 shows the treatment fluid reservoir 670 in a cartridge 672 removed from the applicator body 655. In this variation, at least one fluid inflow channel 675 is provided from the fluid reservoir 670 to the distal end 676 of the applicator body 655. In a typical variation, the open termination 677 of the fluid inflow channel 675 with the proximate to the surface of the rolling member 660 but in should be appreciated that the distal edges of the applicator body 655 may form a seal on the subject's skin as described previously. In another variation, the open termination 677 of the at least one fluid inflow channel 675 can be in an exterior surface of the applicator to allow fluid to be applied to the skin outwardly of the rolling member 660, which is similar to that as shown in FIG. 23 which is further described below. In FIGS. 19 and 21, a single fluid inflow channel 675 is shown but it can be appreciated that a plurality of such channels can be provided with open terminations in the distal end of the applicator.

A key feature of the device of FIGS. 19-21 is the configuration of the components that allows for actuation of the negative pressure source to draw fluid from the cartridge or reservoir 670 through the at least one inflow channel 675 only when the distal tip of the applicator and the rolling member 660 are engaged with the subject's skin. It can be understood that when the distal tip 680 of the applicator body 655 is not in contact with tissue and with the pump assembly 615 being actuated, the only effect will be to pull air around or through the rolling member 660 and into the extraction channel 628 and the interior chamber 640 of the applicator. However, when the distal tip 680 of the applicator is sealed against the subject's tissue surface, then actuation of the pump assembly 615 will apply suction to the distal opening 677 of the fluid inflow channel 675 to draw fluid from the fluid reservoir 670 into the distal tip 680 of the applicator.

Figure 22:
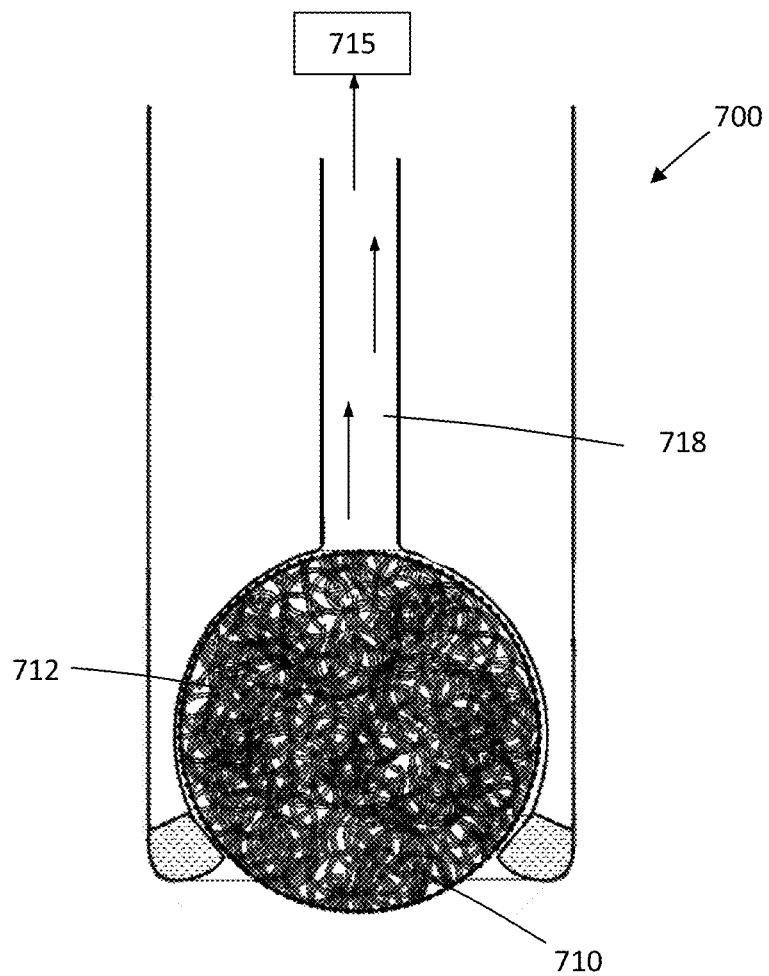
FIG. 22 is an enlarged sectional view a distal portion of another applicator where a spherical rolling member comprises a mesh structure that functions to manipulate tissue as well as functioning as a filter.

FIG. 22 illustrates another variation of working end 700 of an applicator 705 that is similar to previous embodiments except for the rolling member 710 comprises a ball or sphere of a mesh fabricated of fine metal wires, polymer filaments or a combination thereof indicated at 712 that are formed into a spherical shape. The spherical shape can optionally be maintained by adhesives or other suitable means to create a porous spherical member 710. Such a porous spherical member 710 can provide for multiple functions, including comprising a structure with an abrasive surface that can exfoliate skin, providing irregularities in the surface of the rolling member 710 for manipulating tissue and acting as a filter as the negative pressure source 715 suctions treatment fluid through the working end 700 to through outflow channel 718 as shown in FIG. 22. When the mesh rolling member 710 interfaces with a smaller diameter outflow channel 781, it can be appreciated that fluid droplets will be aspirated more readily in a direct path through the rolling member 710 and some liquid will be trapped in interstices of the mesh and fall back onto the skin surface. In other words, such a rolling member 710 can function as a filter and limit the volume of liquid droplets aspirated through the applicator 700. This in turn, can result in a greater volume of treatment media on the skin surface for penetrating the skin by action of the rolling member 710. In a variation, the surfaces of the filaments that make up the rolling member 710 can have a hydrophobic or ultrahydrophobic coating for causing fluid to migrate outwardly or distally under the effect of gravity back onto the tissue surface. In other variations, a combination of hydrophilic and hydrophobic surfaces of the materials of the mesh rolling member 710 can be used to trap and filter liquid droplets from the aspirated media.

FIG. 23 is another variation of applicator working end 725 that similar to that of FIG. 22 with a mesh rolling member 710. In this variation, the extraction channel 728 in the interior of the applicator body 730 includes fluid trapping features 732 for capturing liquid droplets that are aspirated through or around the rolling member 710. The trapping features comprise baffles that extend from opposing sides of the extraction channel 728 or can comprise annular element with non-aligned apertures therein. Such features can have angled surfaces to cause captured fluid droplets to migrate distally under gravity. In the variation of FIG. 23, the captured liquid can enter drain channels 735 that extend to the exterior surface 736 of the applicator body 730 where the liquid can exit the applicator and fall back onto the patient's skin. In a variation, the drain channels 735 can include one-way valves (not shown) such as a sensitive silicone flap valve to allow the weight of the captured fluid to be released through the channels 735, such that the negative pressure source 740 does not affect the one-way valves.

Figure 24:
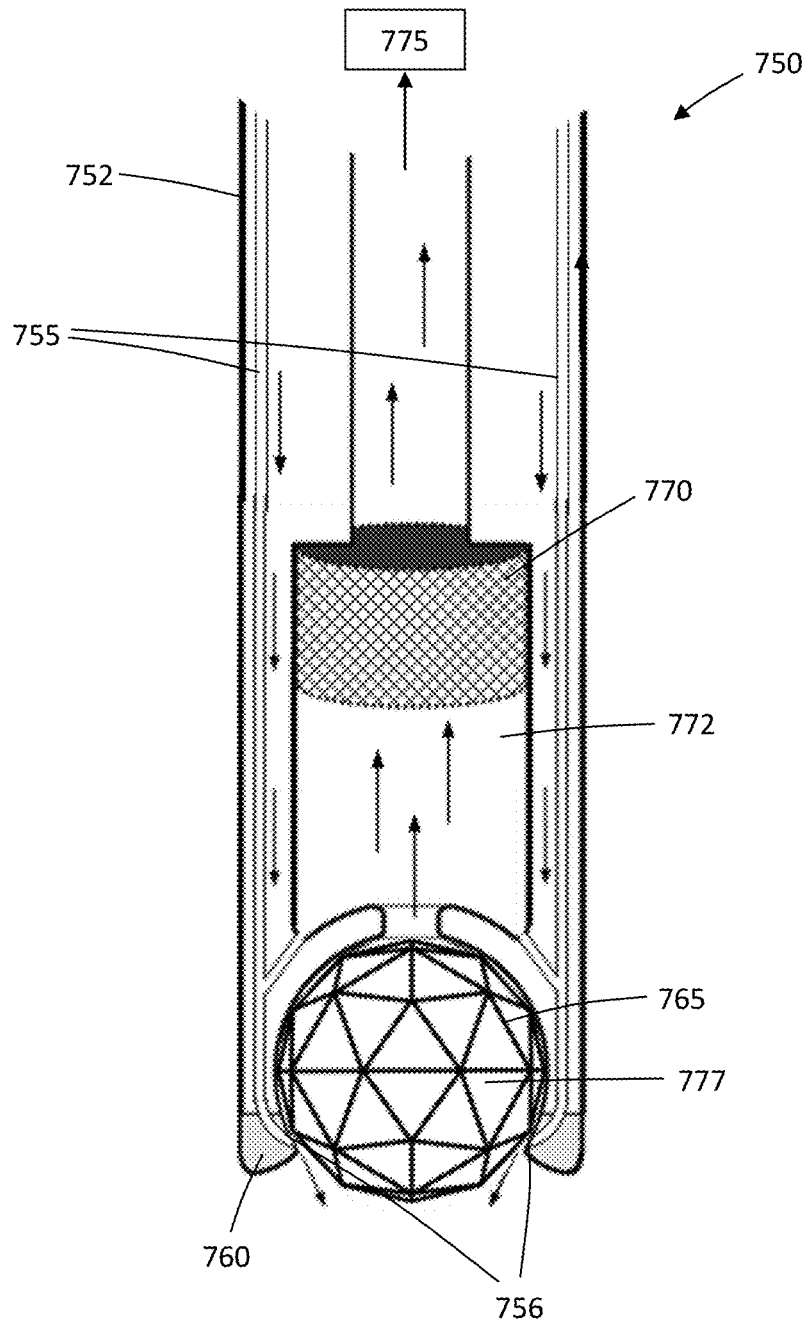
FIG. 24 is a sectional view of the distal portion of another variation of an applicator that carries a faceted rolling member, where the applicator body has fluid inflow channels.
Figure 25:
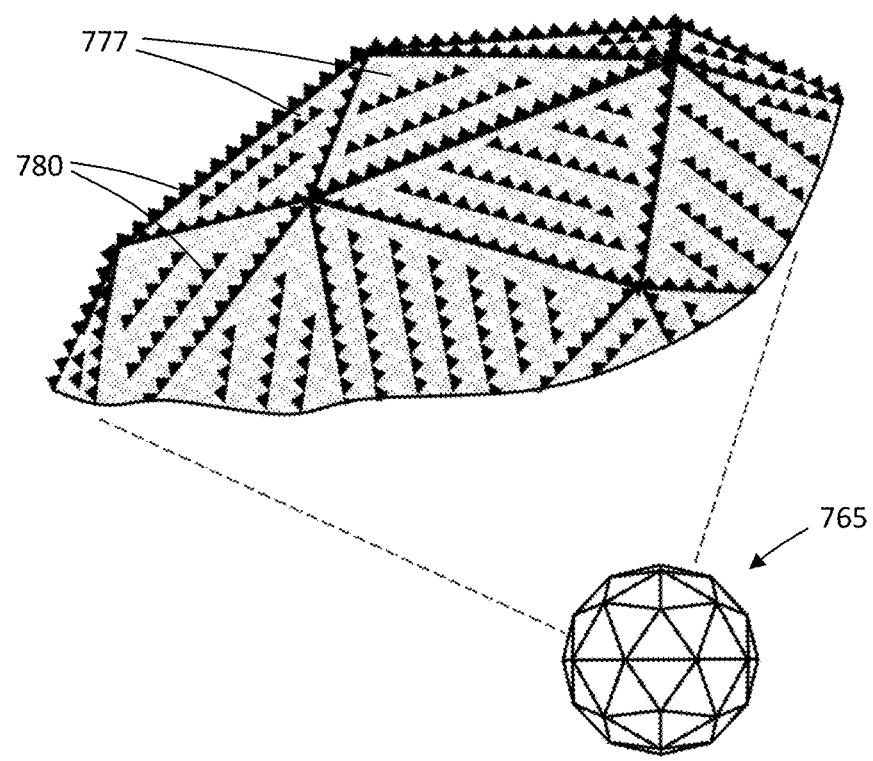
FIG. 25 is an enlarged view of a fragment of the faceted rolling member of FIG. 24 showing diamond particles adhered to the rolling member.

FIG. 24 illustrates another working end 750 of an applicator body 752 that is similar to that of FIGS. 19-21 where the system carries a fluid cartridge and fluid flows are drawn from a fluid cartridge to the inflow channels 755 to open terminations 756 in the distalmost tip 760 of the applicator around the rolling member 765. This variation of working end 750 includes a filter 770 in the extraction channel 772 distal to the pump assembly 775. FIG. 24 further shows a rolling member 765 with facets 777 which is again adapted for rolling over tissue and manipulating tissue. In the enlarged view of a fragment of the rolling member 765 of FIG. 25, it can be seen that the surface of the rolling member 765 is configured with facets 777 that have micro-penetrating elements that can comprise rough or course diamond particles 780. In this variation, the rolling member 765 rolls over tissue and caused micro-penetrations in the tissue surface caused by the manually-applied pressure of the rolling member 765 against tissue in combination with aspiration forces about the facets 777 of the rolling member 765 to enhance penetration of fluid media into subsurface tissues.

Figure 26:
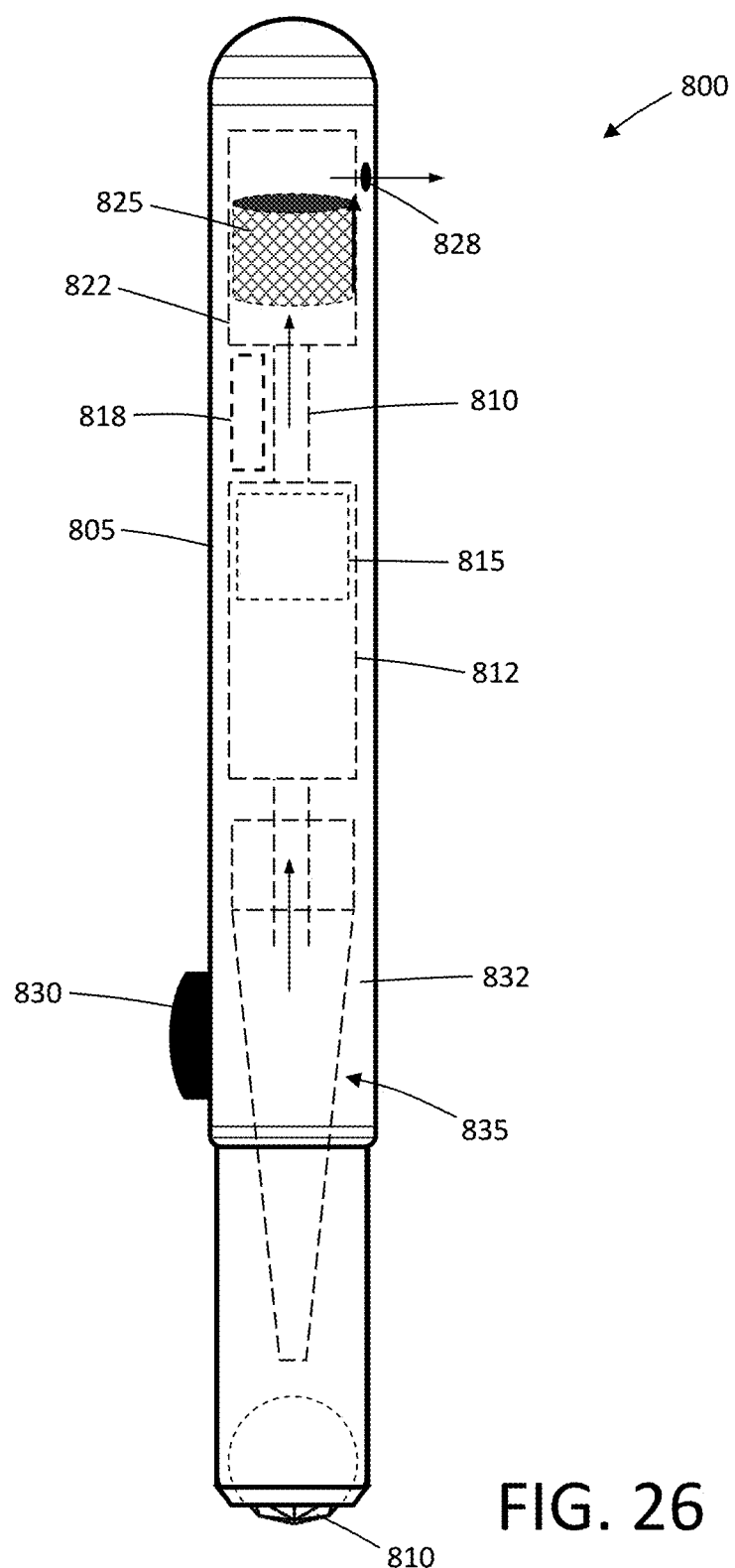
FIG. 26 is an elevational view of another variation of applicator that carries a distal rolling member, a DC motor driven pump assembly, a filter and a cyclonic mechanism for capturing liquid droplets in outflows.
Figure 27:
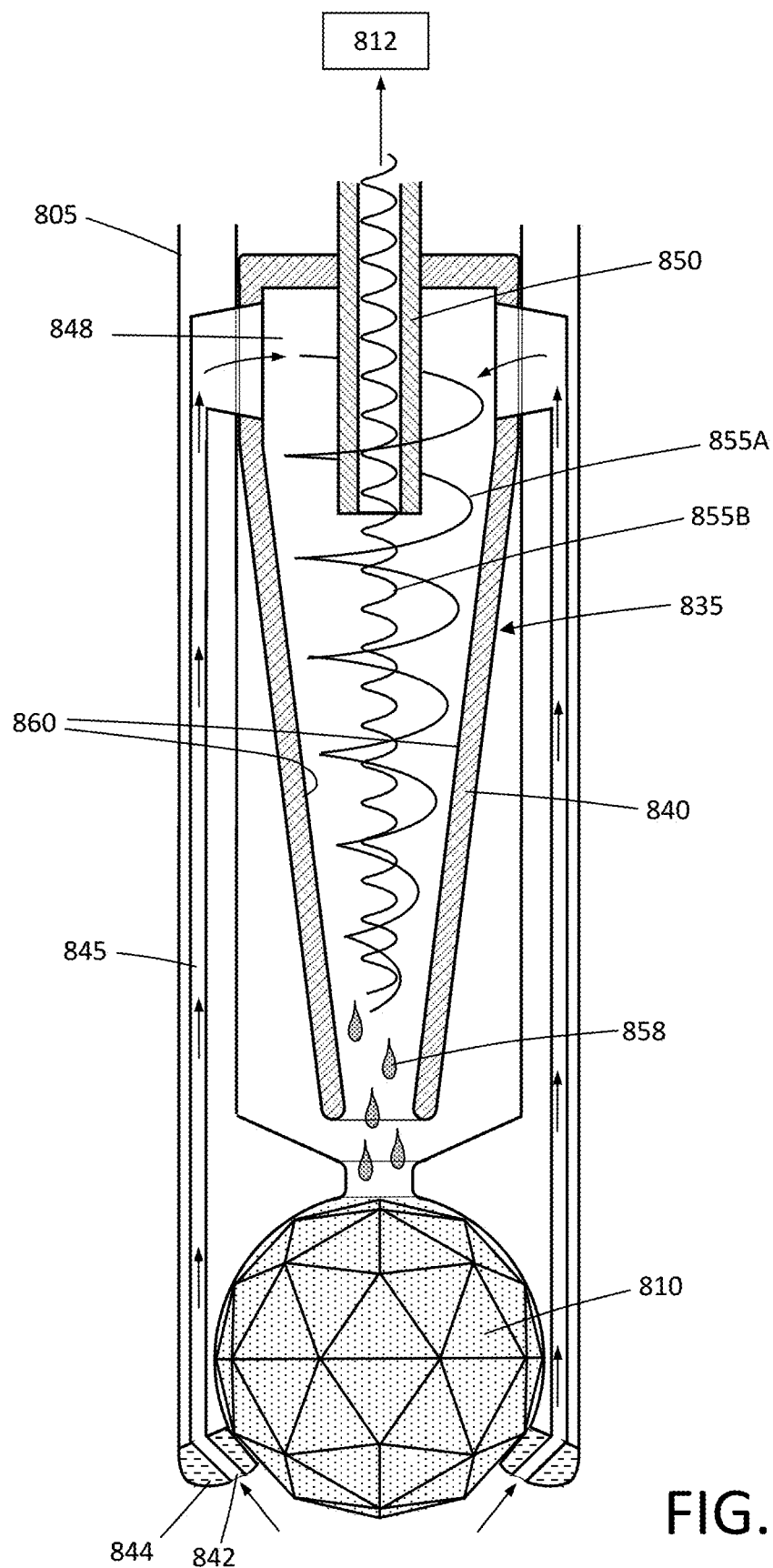
FIG. 27 is an enlarged sectional view of the distal portion of the applicator of FIG. 26 showing the cyclonic mechanism and its method of operation in more detail.

Now turning to FIGS. 26 and 27, another variation of fluid skin treatment device 800 is shown that includes a different mechanism for capturing fluid droplets from treatment media that is being applied to, and aspirated from, a subject's skin. In FIG. 26, it can be seen that the elongate applicator body 805 is similar to previous variations and carries a distal rolling member 810. The applicator body 805 again carries a pump assembly 812 with a DC motor 815 and battery 818 as described previously with the extraction channel 820 and chamber 822 that includes a filter 825 with a vent 828 opening to the exterior of the applicator body 805 for extracting air from the applicator. The device 800 again has a control button 830 that can operate the DC motor 815 at one or more speeds. This variation differs in that the medial portion 832 of the applicator body 805 carries a cyclonic mechanism 835 that is adapted to separate liquid droplets from an outflowing stream of fluid media aspirated from the subject's skin. This variation of treatment device 800 is shown without an internal reservoir or cartridge of treatment fluid and thus the device is adapted for use with topically-applied treatment media where the cyclonic fluid separation of trap mechanism is configured to reduce the removal of treatment fluid and maintain such treatment fluid in or about the skin interface for a longer period of time than would be possible without such a cyclonic mechanism.

FIG. 27 is a sectional view of the applicator body 805 and cyclonic mechanism 835 which includes a conical-shaped cyclone member 840 in the interior of the elongated applicator body 805. Such cyclonic separators are known in industrial applications for separating fluid droplets or particles from air flows or in hydrocyclones used for separating solid from liquids carried in such a fluid flow. As can be seen in FIG. 27, this variation requires substantially fast flows of air through the system so that the negative pressure source or pump 812 does not aspirate fluids through or over the surface of the rolling member 810. In this variation, a plurality of flow ports 842 are positioned in the periphery 844 of the annular distal end of the applicator body 805 with one or more outflow channels 845 leading in the proximal direction that are vented to the proximal end 848 of the conical-shaped member 840. The pump assembly 812 provides negative pressure through the central extractor member 850 which causes the effect of creating a cyclone or circulating flow 855A in the distal direction around the inner wall surfaces 860 of the conical-shaped member 840. This distal cyclonic flow 855A around the wall surfaces 860 then results in a central rotating cyclonic flow e 855B moving in the proximal direction into the central extractor member 850 in the direction of the pump assembly 812. By using this cyclonic mechanism 835, liquid droplets 858 can be extracted from the cyclonic motion of the flowing media in the conical-shaped member 840. In this variation, to provide the required volume of fluid flows, any type of pump assembly 812 may be used, such as a pump assembly in the applicator body 805 or a remote negative pressure source. In general, such an applicator 800 with cyclonic separator may require higher levels of negative pressure and fluid flow rates than previous variations. In all other respects, use of the rolling member 810 at the distal end of the applicator body 805 functions as previously described to manipulate a subject's skin and enhance fluid penetration into subsurface tissue over the targeted site while separating liquid droplets from the outflows.

Figure 28:
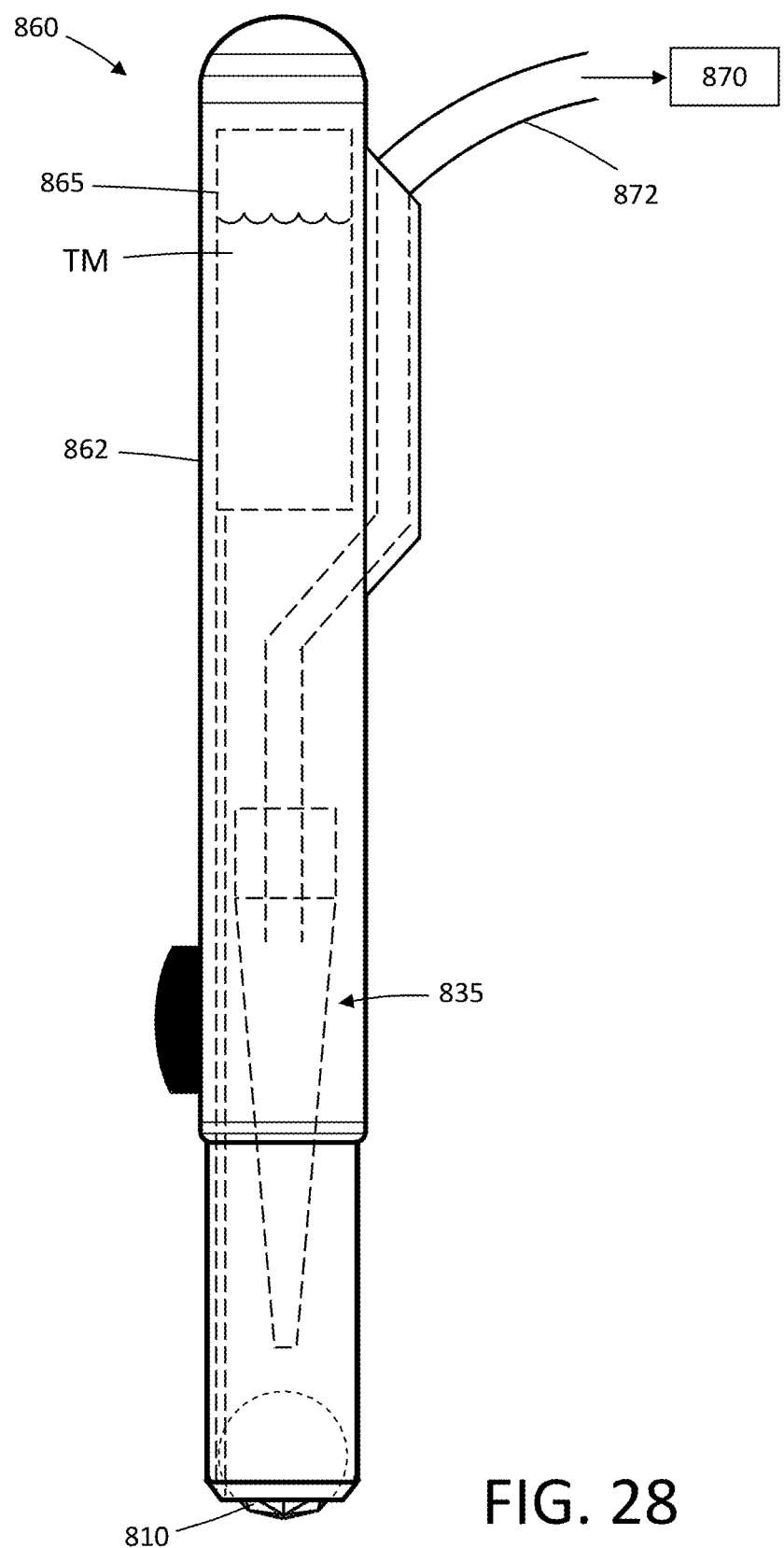
FIG. 28 is an elevational view of another variation of applicator that includes a fluid reservoir carried by the applicator body and a cyclonic mechanism as in FIGS. 26 and 27 with a remote negative pressure source.

FIG. 28 shows another variation of an applicator 860 with an elongate body 862 that is similar to the previous variation of FIGS. 26 and 27. In this variation, the cyclone mechanism 835 functions as described previously. The device of FIG. 28 differs in that a fluid reservoir 865 is provided in the applicator body 862 to carry a treatment fluid TM. Also, in this variation, the negative pressure source 870 is remote and connected by flexible tubing 872 to the applicator body 862. In another variation (not shown), an applicator similar to that of FIGS. 26 and 28 can be adapted to carry all of the components described above in a single hand-held device. That is, the applicator body can be configured with a cyclonic mechanism, a pump assembly, a battery, a filter and a treatment fluid reservoir.

Figures 29, 30:
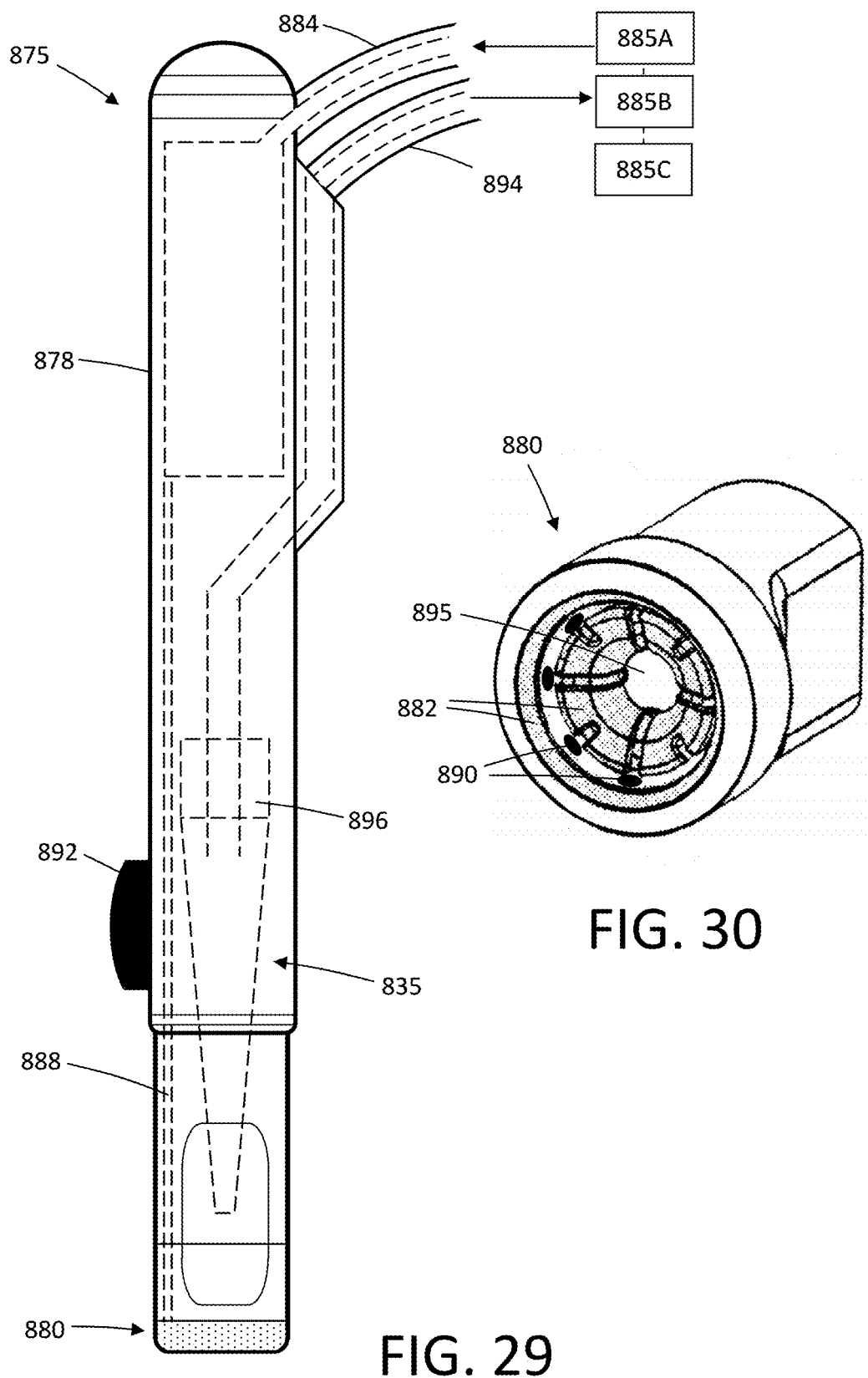
FIG. 29 is an elevational view of another variation of applicator that includes a cyclonic mechanism with distal tip adapted for tissue manipulation or microdermabrasion.
FIG. 30 is an enlarged view of the detachable distal tip of the applicator of FIG. 29.

FIGS. 29 and 30 illustrate yet another variation of a skin treatment device 875 that carries a cyclonic mechanism 835 as described previously in the applicator body 878. However, the device of FIG. 29 does not utilize a distal rolling member but has a distal tip 880 shown in an enlarged view in FIG. 30. The distal tip 880 is adapted for microdermabrasion and has sharp edges or abrasive portions 882 for abrading skin and exfoliating skin. In this variation, the device 875 may or may not carry a fluid reservoir and a pump assembly within the applicator body 878. FIG. 29 shows that flexible tubing 884 is coupled to the applicator body 878 for supplying fluid from a fluid source 885A to the patient's skin through at least one inflow channel 888 to open terminations 890 in the distal tip 880 (see FIG. 30). A negative pressure source 885B is provided with actuator switch 892 in the applicator body connected to a remote controller 885C to operate the negative pressure source 885B and optionally a positive pressure fluid source 885A. FIG. 29 shows that the conical cyclone mechanism 835 communicates with the remote negative pressure source 888B through tubing 894 that is adapted to draw fluid through the central aperture 895 in the distal tip 880 and then through flow channels (not shown) to the proximal portion 896 of the conical cyclonic mechanism 835 which allows for capture and re-deployment of fluid droplets to the subject's skin as described previously. In one variation, the actuator switch 892 is configured for selecting among a plurality of different negative pressure levels and further for selecting between various pulsed negative pressure duty cycles. In a variation used for treatments of hair loss, the distal tip 880 of FIG. 30 can be configured for tissue manipulation with greater surface irregularities and less abrasive features. The distal tip 880 of FIG. 30 and similar fluid-assisted dermabrasion tips and systems are described in the author's U.S. Pat. Nos. 6,641,591 and 6,387,103 which are incorporated herein by reference.

In general, a method of the invention comprises causing negative pressure in the applicator which is turn caused liquid treatment media to be entrained in outflows through the applicator from the targeted skin. The method further comprises capturing the entrained liquid treatment media from such outflows and returning the captured treatment media to the targeted skin.

Figures 31, 32A, 32B:
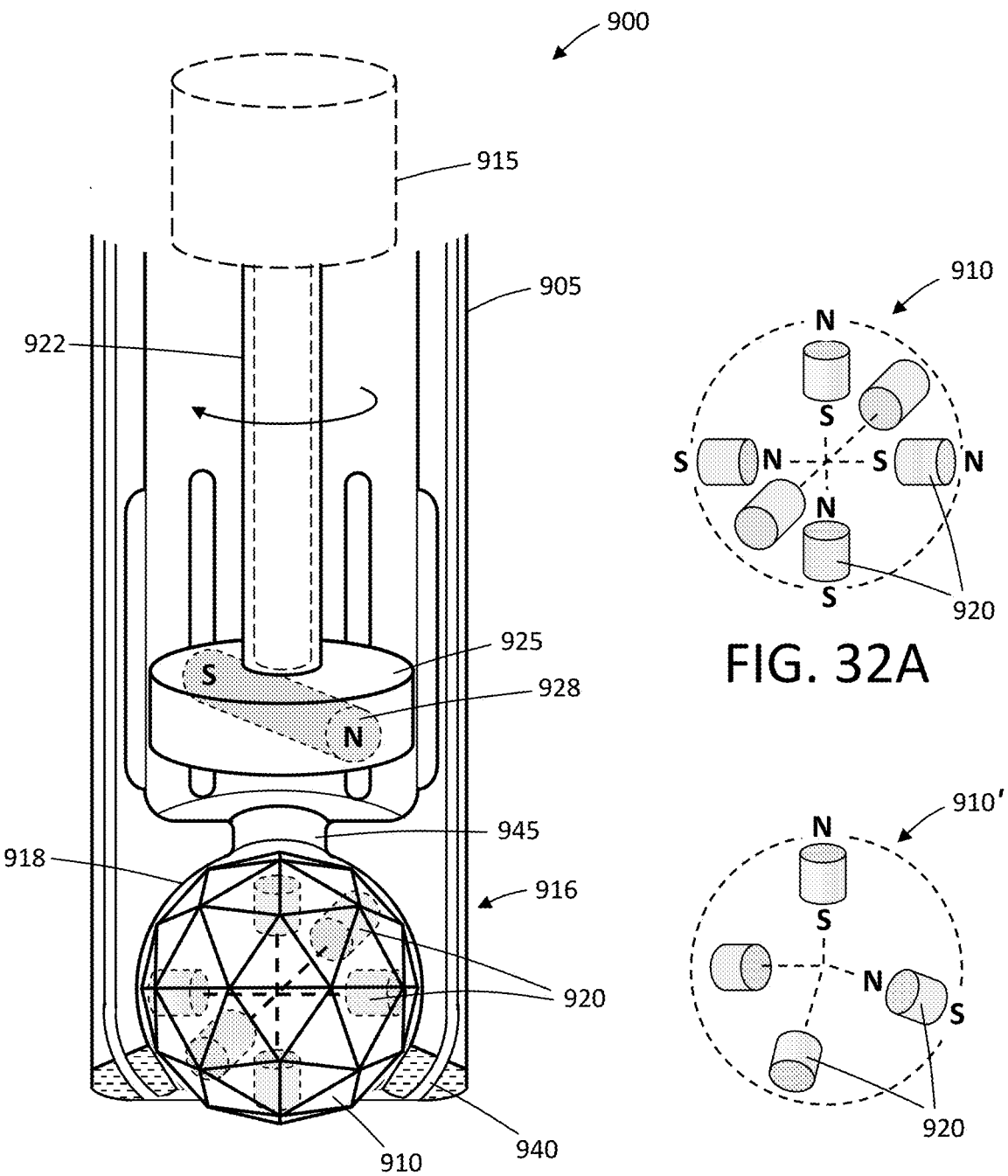
FIG. 31 is a sectional view of another variation of applicator working end that includes a motor driven rotor with rare earth magnets therein that are adapted rotates or influence a rolling member that carries magnets.
FIG. 32A is an enlarged schematic view of rolling member of FIG. 31.
FIG. 32B is a schematic view of another variation of rolling member similar to that of FIG. 31 with a different configuration of magnets.

Now turning to FIGS. 31, 32A and 32B, another variation of a skin treatment device 900 with applicator body 905 is shown which is adapted for applying rotational forces to a rolling member 910 during use. In previous variations, a method of using the rolling member 910 was described in manipulating tissue to enhance fluid penetration into subsurface tissues. In all previous variations, such a rolling member was actively moved or rolled by movement of the applicator and rolling member over tissue together with negative pressure provided by the negative pressure source. The variation of FIG. 31 differs in that the rolling member 910 during use can be moved, agitated, or prevented from rolling by motor drive 915 as can be understood in FIG. 31. In FIG. 31, the distal end 916 of the applicator body 905 again is configured with a receiving space 918 for receiving the rolling member 910 which can be of any type described previously. However in the variation of FIG. 31, the rolling member 910 carries at least one magnet, and is shown with a plurality of rare earth magnets 920 or magnetic responsive materials that respond to magnetic fields created within the applicator body 905 proximate to the rolling member 910. In one variation, as shown in FIG. 31, the motor drive 915 rotates the motor shaft 922 that is coupled to a rotating collar 925 with at least one rare earth magnet 928 therein, for example, a neodynium magnet. Upon motor-driven rotation of the collar 925 and rotation of the North and South poles of the magnet 928 will influence and rotate the rolling member 910 in the absence of resistance created by engagement of the rolling member 910 with a subject's skin. In some variations, the motor drive 915 and magnets 920 and 928 can be sufficiently strong to rotate the rolling member 910 when in contact with tissue to abrade, exfoliate or otherwise manipulate tissue. In other variations, activation of the motor drive 915 may be pulsed to stop or inhibit rotation of the rolling member 910 as it is rolled over a targeted site. By such magnetic influence of the rolling resistance of rolling member 910, any sharp features on the surface of the rolling member 910 can penetrate tissue which can enhance fluid penetration therein. Inflow and outflow channels 940 are 945 are shown in FIG. 31 which operate as described previously. It should be appreciated that the inflow and outflow channel also can be reversed as described in some variation above, depending on whether the device is configured for negative pressure around the rolling member 910 or fluid delivery around the rolling member 910.

FIG. 32A shows the rolling member 910 of FIG. 31 is schematic view and FIG. 32B shows rolling member 910' with a different arrangements of magnets 920 or magnetic responsive materials therein that can be influenced by the rotating magnetic collar 925. Any number of magnets in various orientation may be used. In another variation, one or more electromagnets can be provided around a rolling member 910 which can be activated in sequence to cause similar effects or rotating or influencing rotation of a rolling member.

In other variations, an ultrasound wave generator such as a piezoelectric crystal can be provided in the distal tip of the applicator to deliver pressure waves at ultrasonic speeds to the skin, for example, in the range of 1 Mhz to 6 Mhz to enhance fluid absorption. In another variation, the working end can include components and electrodes for delivering electrical current through the rolling member or the distal periphery of the roller housing to the skin of a patient to enhance fluid penetration. In a further variation, the LEDs as in FIG. 11 can transmit UV light to kill bacteria. In other variations, the applicator body can carry a motor-driven pump to provide the negative pressure on demand, where the motor can be powered by a battery carried in the applicator body. In another variation, a treatment fluid source can be provided to deliver a treatment fluid through the applicator body to the skin surface during use, where the treatment fluid source can be a cartridge carried by the applicator or a remote source coupled to the applicator by a tubing set. While the figures above illustrate a spherical rolling member, it should be appreciated that a cylindrical rolling member falls within the scope of the invention where the features of cylindrical and spherical rolling members, cooperating receiving spaces and distal applicator peripheries can be similar.

While the invention has been described for delivery of treatment media to a subject's skin and lips largely for skin rejuvenation and cosmetic purposes, the negative pressure applicator can also be use for delivery of any type of pharmaceuticals through an exposed tissue surface, such as analgesics, anti-inflammatory drugs, vaccines, stimulants, hormones and the like.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed and the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A method for treating hair loss in a targeted tissue of a subject, the method comprising:
    applying a treatment media configured to aid in hair growth to targeted tissue of the subject;
    contacting the targeted tissue with an applicator; and
    drawing a negative pressure in the applicator while moving the applicator when in contact with the targeted tissue to transiently apply the negative pressure in a subsurface tissue to enhance penetration of the treatment media into the targeted tissue.

2. The method of claim 1, where the treatment media includes a substance selected from a group consisting of finasteride, minoxidil, corticosteroid, dutasteride, nanoxidil, redensyl, capixyl, procapil psoralen and a combination thereof.

3. The method of claim 1, where drawing the negative pressure comprises pulsing the negative pressure.

4. The method of claim 1, wherein the negative pressure comprises includes actuating a vacuum pump mechanism.

5. The method of claim 1, further comprising manipulating the targeted tissue with the applicator to enhance penetration of the treatment media therein.

6. The method of claim 5, wherein manipulating the targeted tissue includes at least one of compressing, stretching, tensioning, exfoliating and piercing a tissue surface with surface features of the applicator.

7. The method of claim 5, wherein the applicator includes a rolling member and manipulating the targeted tissue comprises rolling the rolling member on the targeted tissue.

8. The method of claim 7, wherein the negative pressure is provided through a flow path around the rolling member.

9. The method of claim 7, wherein the negative pressure causes a suction of treatment media in a circuitous path over the targeted tissue about a surface feature of the rolling member to enhance penetration of the treatment media in the targeted tissue.

10. The method of claim 1, further comprising moving the applicator over the targeted tissue.

11. The method of claim 10, wherein the applicator comprises a rolling member and where moving the applicator comprises rolling the rolling member on the targeted tissue to exfoliate the targeted tissue with a surface feature of the rolling member to enhance penetration of the treatment media in the targeted tissue.

12. The method of claim 1, wherein a distal periphery of the applicator contacts tissue to seal the negative pressure over the targeted tissue.

13. The method of claim 1, further comprising irradiating the targeted tissue with light wavelengths from a light emitter carried by the applicator.

14. The method of claim 1, further comprising applying energy from an ultrasound emitter to the tissue, where the ultrasound emitter is carried by the applicator.

15. A device for treatment of a subject's skin or lips, comprising:
    an applicator body having a distal applicator tip;
    the applicator tip including an inflow path channel and an outflow path;
        a liquid media source in communication with the inflow path;
    a negative pressure source in communication the outflow path configured to pull a negative pressure in the applicator body;
    a collector in the outflow path adapted to capture liquid media from a flow therein; and
    a rolling member rotatably exposed at the applicator tip, the rolling member comprising a plurality of surface discontinuities in a surface of the rolling member such that the plurality of surface discontinuities permit transient application of the negative pressure to the subject's skin or lips.

16. The device of claim 15, wherein the collector comprises structure selected from a group consisting of a cyclonic mechanism, a baffle arrangement, a filter, and a combination thereof.

17. The device of claim 15, wherein the applicator body carries a pump comprising the negative pressure source.

18. The device of claim 15, wherein the applicator body carries a reservoir comprising the liquid media source.

19. A method for treating a targeted skin of a subject, comprising:
    providing an applicator carrying a motor-driven pump assembly for providing negative pressure through a distal tip of the applicator;
    applying a treatment media to the targeted skin;
    contacting the targeted skin with the distal tip of the applicator to manipulate the targeted skin; and
    drawing negative pressure in the applicator while moving the distal tip in contact with the targeted skin such that moving the distal tip causes transient application of negative pressure at a plurality of locations on the targeted skin and on a corresponding subsurface tissue, which enhances penetration of the treatment media into the targeted skin.

20. The method of claim 19, wherein contacting the targeted skin with the applicator to manipulate the targeted skin includes at least one of compressing, stretching, tensioning, exfoliating and piercing a tissue surface with the applicator.

21. The method of claim 19, wherein the applicator further comprises a rolling member at a distal end of the applicator and where manipulating the targeted skin comprises rolling the rolling member over a surface of the targeted skin and where causing transient application of negative pressure occurs at a plurality of locations about the surface of the rolling member while rolling.

22. The method of claim 19, wherein drawing negative pressure results in treatment media being entrained in outflows through the applicator from the targeted skin.

23. The method of claim 22, further comprising capturing entrained liquid treatment media from an outflow.

24. The method of claim 22, further comprising capturing the treatment media is provided by at least one of a cyclonic mechanism, a baffle arrangement and a filter.

25. The method of claim 19, wherein the applicator further comprises a reservoir of a treatment fluid carried by the applicator, and where applying treatment media comprises delivering the treatment fluid using the applicator.

26. The method of claim 19, wherein applying treatment media comprises causing a flow of fluid around or through a surface of a rolling member carried at a distal end of the applicator.

27. The method of claim 19, wherein causing negative pressure results in outflows around or through a surface of a rolling member carried at a distal end of the applicator.

28. A method for treating hair loss in a targeted tissue of a subject, the method comprising:
    applying a treatment media configured to aid in hair growth to targeted tissue of the subject;
    contacting the targeted tissue with an applicator having a rolling member;
    rolling the rolling member on the targeted tissue on the targeted tissue with the applicator to enhance penetration of the treatment media therein by at least one of compressing, stretching, tensioning, exfoliating and piercing a tissue surface with surface features of the applicator;
    drawing a negative pressure through a flow path around the rolling member when in contact with the targeted tissue to transiently apply the negative pressure in a subsurface tissue to enhance penetration of the treatment media into the targeted tissue.

29. A method for treating hair loss in a targeted tissue of a subject, the method comprising:
    applying a treatment media configured to aid in hair growth to targeted tissue of the subject;
    contacting the targeted tissue with an applicator having a rolling member; and
    moving the applicator over the targeted tissue by rolling the rolling member on the targeted tissue to exfoliate the targeted tissue with a surface feature of the rolling member to enhance penetration of the treatment media in the targeted tissue;
    drawing a negative pressure about the applicator when in contact with the targeted tissue to transiently apply the negative pressure in a subsurface tissue to enhance penetration of the treatment media into the targeted tissue.

30. A method for treating a subject's skin, comprising:
    providing an applicator carries a motor-driven pump assembly for providing negative pressure in the applicator;
    applying treatment media to a targeted skin of a subject;
    contacting the targeted skin with an applicator to manipulate the targeted skin; and
    drawing negative pressure about the applicator while moving the applicator in contact with the targeted tissue to transiently cause negative pressure in a subsurface tissue to enhance penetration of the treatment media into the targeted skin and results in outflows around or through a surface of a rolling member carried at a distal end of the applicator.

\* \* \* \* \*

UNITED STATES PATENT AND TRADEMARK OFFICE
CERTIFICATE OF CORRECTION

PATENT NO. : 11,110,260 B1
APPLICATION NO. : 17/010161
DATED : September 7, 2021
INVENTOR(S) : Shadduck Page 1 of 1

It is certified that error appears in the above-identified patent and that said Letters Patent is hereby corrected as shown below:

In the Claims

Column 23, Line 20:
Replace "the applicator tip including an inflow path channel and an" with --the applicator tip including an inflow path and an--

Signed and Sealed this
Twenty-fifth Day of January, 2022

Drew Hirshfeld
*Performing the Functions and Duties of the*
*Under Secretary of Commerce for Intellectual Property and*
*Director of the United States Patent and Trademark Office*